US009583335B2

(12) United States Patent
Dussarrat et al.

(10) Patent No.: US 9,583,335 B2
(45) Date of Patent: *Feb. 28, 2017

(54) METHOD OF FORMING DIELECTRIC FILMS, NEW PRECURSORS AND THEIR USE IN SEMICONDUCTOR MANUFACTURING

(71) Applicant: L'Air Liquide, Société Anonyme pour l'Etude et l'Exploitation des Procédés Georges Claude, Paris (FR)

(72) Inventors: Christian Dussarrat, Tokyo (JP); Nicolas Blasco, Grenoble (FR); Audrey Pinchart, Labege (FR); Christophe Lachaud, Sain Michel sur Orge (FR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 311 days.

This patent is subject to a terminal disclaimer.

(21) Appl. No.: 14/187,712

(22) Filed: Feb. 24, 2014

(65) Prior Publication Data

US 2014/0242812 A1  Aug. 28, 2014

Related U.S. Application Data

(63) Continuation-in-part of application No. 12/303,169, filed as application No. PCT/EP2007/052507 on Mar. 16, 2007, now Pat. No. 8,668,957.

(30) Foreign Application Priority Data

Jun. 2, 2006  (WO) ................ PCT/EP2006/062893

(51) Int. Cl.
*C23C 16/40* (2006.01)
*H01L 21/02* (2006.01)

(52) U.S. Cl.
CPC ........ *H01L 21/02205* (2013.01); *C23C 16/40* (2013.01); *C23C 16/405* (2013.01);
(Continued)

(58) Field of Classification Search
None
See application file for complete search history.

(56) References Cited

U.S. PATENT DOCUMENTS 5,527,752 A   6/1996  Reichle et al.
5,846,895 A   12/1998 Gila et al.
(Continued)

FOREIGN PATENT DOCUMENTS

EP  0 757 064   5/1997
EP  1 067 595   1/2001
(Continued)

OTHER PUBLICATIONS

Jones et al.; Some Recent Developments in the MOCVD and ALD of high-K dielectric oxides; J. Mater. Chem., 14; 3101-3112; 14; 2004.*
(Continued)

*Primary Examiner* — Guinever S Gregorio
(74) *Attorney, Agent, or Firm* — Patricia E. McQueeney

(57) ABSTRACT

Method of deposition on a substrate of a dielectric film by introducing into a reaction chamber a vapor of a precursor selected from the group consisting of $Zr(MeCp)(NMe_2)_3$, $Zr(EtCp)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)(NEt_2)_3$, $Zr(EtCp)(NEt_2)_3$, $ZrCp(NEt_2)_3$, $Zr(iPr_2Cp)(NMe_2)_3$, $Zr(tBu_2Cp)(NMe_2)_3$, $Hf(MeCp)(NMe_2)_3$, $Hf(EtCp)(NMe_2)_3$, $HfCp(NMe_2)_3$, $Hf(MeCp)(NEtMe)_3$, $Hf(EtCp)(NEtMe)_3$, $HfCp(NEtMe)_3$, $Hf(MeCp)(NEt_2)_3$, $Hf(EtCp)$
(Continued)

(NEt$_2$)$_3$, HfCp(NEt$_2$)$_3$, Hf(iPr$_2$Cp)(NMe$_2$)$_3$, Hf(tBu$_2$Cp)(NMe$_2$)$_3$, and mixtures thereof; and depositing the dielectric film on the substrate.

19 Claims, 9 Drawing Sheets

(52) U.S. Cl.
CPC .... *H01L 21/0228* (2013.01); *H01L 21/02181* (2013.01); *H01L 21/02189* (2013.01); *H01L 21/02271* (2013.01)

(56) References Cited

U.S. PATENT DOCUMENTS

| | | |
|---|---|---|
| 5,861,352 A | 1/1999 | Gila et al. |
| 5,970,604 A | 10/1999 | Person et al. |
| 6,001,742 A | 12/1999 | Chang |
| 6,197,683 B1 | 3/2001 | Kang et al. |
| 6,268,448 B1 | 7/2001 | Collins et al. |
| 6,445,023 B1 | 9/2002 | Vaartstra et al. |
| 6,548,424 B2 | 4/2003 | Putkonen |
| 6,669,990 B2 | 12/2003 | Min et al. |
| 6,689,675 B1 | 2/2004 | Parker et al. |
| 6,743,473 B1 | 6/2004 | Parkhe et al. |
| 6,858,547 B2 | 2/2005 | Metzner et al. |
| 6,984,591 B1 | 1/2006 | Buchanan et al. |
| 7,108,747 B1 | 9/2006 | Leskela et al. |
| 7,157,780 B2 | 1/2007 | Harada |
| 7,666,752 B2 | 2/2010 | Kudelka et al. |
| 7,833,913 B2 | 11/2010 | Clark |
| 2001/0001949 A1 | 5/2001 | Westmoreland et al. |
| 2004/0198069 A1 | 10/2004 | Metzner et al. |
| 2004/0235312 A1 | 11/2004 | Loftin et al. |
| 2005/0056219 A1 | 3/2005 | Dip et al. |
| 2005/0218462 A1 | 10/2005 | Ahn et al. |
| 2005/0260357 A1 | 11/2005 | Olsen et al. |
| 2006/0046521 A1 | 3/2006 | Vaartstra et al. |
| 2006/0062910 A1* | 3/2006 | Meiere ............... C01G 27/04 427/226 |
| 2006/0062917 A1 | 3/2006 | Muthukrishnan et al. |
| 2006/0097305 A1 | 5/2006 | Lee |
| 2006/0228888 A1 | 10/2006 | Lee et al. |
| 2006/0269667 A1 | 11/2006 | Ma et al. |
| 2007/0001231 A1 | 1/2007 | Currie |
| 2008/0102205 A1 | 5/2008 | Barry et al. |
| 2008/0308793 A1 | 12/2008 | Jeong et al. |
| 2009/0074983 A1 | 3/2009 | Heys et al. |
| 2009/0203222 A1 | 8/2009 | Dussarrat et al. |
| 2009/0311879 A1 | 12/2009 | Blasco et al. |
| 2011/0207337 A1 | 8/2011 | Dussarrat et al. |

FOREIGN PATENT DOCUMENTS

| | | |
|---|---|---|
| EP | 1 524 299 | 4/2005 |
| JP | 11 307519 | 11/1999 |
| JP | 11 514798 | 12/1999 |
| JP | 2001 102326 | 4/2001 |
| JP | 2001 355070 | 12/2001 |
| JP | 2002 069641 | 3/2002 |
| JP | 2002 093803 | 3/2002 |
| JP | 2002 093804 | 3/2002 |
| JP | 2004 507551 | 3/2004 |
| JP | 2004 300579 | 10/2004 |
| JP | 2004 349710 | 12/2004 |
| JP | 2005 104994 | 4/2005 |
| JP | 2005 171291 | 6/2005 |
| JP | 2005 209766 | 8/2005 |
| JP | 2005 351450 | 12/2005 |
| KR | 102007121281 | 12/2007 |
| KR | 102008101040 | 11/2008 |
| WO | WO 96 27032 | 9/1996 |
| WO | WO 96 35726 | 11/1996 |
| WO | WO 97 49105 | 12/1997 |
| WO | WO 02 18394 | 3/2002 |
| WO | WO 2003 035926 | 5/2003 |
| WO | WO 2004 010469 | 1/2004 |
| WO | WO 2005 113852 | 12/2005 |
| WO | WO 2007 141059 | 6/2006 |
| WO | WO 2006 131751 | 12/2006 |
| WO | WO 2007 005088 | 1/2007 |
| WO | WO 2007 011973 | 1/2007 |
| WO | WO 2007 030673 | 3/2007 |
| WO | WO 2007 066546 | 6/2007 |
| WO | WO 2007 140813 | 12/2007 |
| WO | WO 2007 141059 | 12/2007 |
| WO | WO 2009 106433 | 9/2009 |

OTHER PUBLICATIONS

Becker, J.S. et al., "Atomic layer deposition of hafnium and zirconium nitrides", Chem. Mater. 2004, 16, 3497-3501.

Cano, J. et al., "Neutral and cationic [bis(n1-amidosilyl)-n5-cyclopentadienyl]titanium and -zirconium complexes: synthesis, x-ray molecular structures and DFT calculations", Eur. J. Inorg. Chem. 2003 2463-2474.

Carta, G. et al., "Thermal properties of volatile organohafnium precursors for HfO$_2$ MOCVD processes," Electrochemical Society Proceedings vol. 2005-09, pp. 260-267.

Caymax, M. et al., "High-k materials for advanced gate stack dielectrics: a comparison of ALCVD and MOCVD as deposition technologies," 2003 Materials Research Society Symposium Proceedings, vol. 765, pp. 47-58.

Chandra, G. et al. "Amido-derivatives of metals and metalloids. Part VI. Reactions of titanium(IV), zirconium(IV), and hafnium(IV) amides with protic compounds," Journal of Chemical Society (A), 1968, pp. 1940-1945.

Chang, H.S. et al. "Electrical and physical properties of HfO$_2$ deposited via ALD using Hf(OtBu)$_4$ and ozone atop Al$_2$O$_3$," Electrochem. Solid-State Letters, 7 (6) F42-F44 (2004).

Ciruelo, G. et al., "Synthesis and reactivity of new silyl substituted monocyclopentadienyl zirconium complexes. X-ray molecular structure of [Zr(N$^5$—C$_5$H$_4$(SiMe$_2$CH$_2$Ph))(CH$_2$Ph)$_3$]", Journal of Organometallic Chemistry 547 (1997) 287-296.

Codato, S. et al. "MOCVD growth and characterization of ZrO2 thin films obtained from unusual organo-zirconium precursors," Chemical Vapor Deposition, Wiley-VCH Verlag, Weinheim, Germany, vol. 11, No. 11, 1999, pp. 159-164.

Cotton, S.A. "Ti, Ar, Hf," Annu. Rep.Prog. Chem., Sect. A: Inorganic Chemistry, 1993, 90, pp. 119-130.

Hausmann, D.M. et al. "Atomic layer deposition of hafnium and zirconium oxide using metal amide precursors," Chem., Mater. 2002, 14, 4350-4353.

Herrmann, W.A. et al. "Volatile metal alkoxides according to the concept of donor functionalization," Angew. Chem. Int. Ed. Engl. 1995, 34, pp. 2187-2206.

Irigoyen, A.M. et al., Synthesis and characterization of chlorobis(dialkylamido) and alkylbis(dialkylamido) derivatives of [(n$^5$-C$_5$Me$_5$)MCl$_3$](M=Ti, Zr), Journal of Organometallic Chemistry, 494 (1995) 255-259.

Juppo, M. et al. "In situ mass spectrometry study on surface reactions in atomic layer deposition of Al$_2$O$_3$ thin films from trimethylaluminum and water," Langmuir 2000, 16, pp. 4034-4039.

Jutzi, P. et al., "Halbsandwich-Komplexe der Elemente Titan and Zirconium mit dem (Diisopropylaminoethyl) cyclopentadienyl-Ligand: Molekülstruktur von [(C$_5$H$_4$CH$_2$CH$_2$N(H)$^i$Pr$_2$)ZrCl$_3$]$^+$Cl$^-$·2CH$_3$OH", Journal of Organometallic Chemistyr 533 (1997), 237-245.

Kawahara, T. et al. "Effect of Hf source, oxidizing agents, and NH$_3$/Ar plasma on the properties of HfAlO$_x$ films prepared by atomic layer deposition," J. Appl. Phys., vol. 43, No. 7A, 2004, pp. 4129-4134.

Kim, M.-S. et al., "ALD analyses of HfCl4 + O3 and HfCl4 + H2O by mass spectroscopy," Electrochemical Society Proceedings vol. 2005-05, pp. 397-403.

(56) References Cited

OTHER PUBLICATIONS

Kukli, K. et al., "Atomic layer deposition of hafnium dioxide films from 1-methoxy-2-methyl-2-propanolate complex of hafnium," Chem Mater. 2003, 15, pp. 1722-1727.
Kukli, K. et al., "Influence of growth temperature on properties of zirconium dioxide films grown by atomic layer deposition," Journal of Applied Physics, 2002, 92, p. 1833-1840.
Lehn, J.-S. et al., "New precursors for the DVD of zirconium and hafnium oxide films," Chem Vap. Deposition 2006, 12, pp. 280-284.
Niinisto, J. et al., "Development of novel processes for atomic layer deposition of high-k dielectrics", $72^{nd}$ Annual Meeting of the DPG, Feb. 27, 2008, Berlin.
Niinisto, J. et al. "In situ quadrupole mass spectrometry study of atomic-layer deposition of ZrO2 using $Cp_2Zr(CH_3)_2$ and water," Langmuir, 7321, 21, 2005.
Pinchart, A. et al., "Novel thermally-stable hafnium and zirconium ALD precursors", IEEE/SEMI Advanced Semiconductor Manufacturing Conference (ASMC) 2007.
Potter, R.J. et al., "Deposition of $HfO_2$, $Gd_2O_3$ and $PrO_x$ by liquid injection ALD techniques," Chem. Vap. Deposition 2005, 11, No. 3, pp. 159-169.
Putkonen, M. et al., "Organometallic precursors for atomic layer deposition," Top Organomet Chem, 2005, 9, pp. 125-145.
Putkonen, M. et al. "Zirconia thin films by atomic layer epitaxy. A comparative study on the use of novel precursors with ozone," J. Mater. Chem., 3141, 11, 2001.
Rie, K.-T. et al., "Plasma assisted CVD for low temperature coatings to improve the wear and corrosion resistance," Surface and Coatings Technology, 1996, 86-87, pp. 498-506.
Ritala, M. et al., "Atomic layer deposition," Ch. 2, Handbook of Thin Film Materials, H.S. Nalwa, ed., vol. 1, "Deposition and Processing of Thin Films," Academic Press, San Diego, CA, 2002.
Rogers, J.S. et al., "Fulvene to cyclopentadienyl conversion with homoleptic complexes of zirconium and hafnium", Organometallics 1999 18, 3976-3980.
Schneider, H. et al. "Immobilization of $\eta^5$-cyclopentadienyltris(dimethylamido)zirconium polymerization catalysts on a chlorosilane- and HMDS-modified mesoporous silica surface: A new concept for supporting metallocene amides towards heterogenous single-site-catalysts," Journal of Molecular Catalysts A; Chemical 170 (2001) pp. 127-141.
Senzaki, Y. et al. "Atomic layer deposition of hafnium oxide and hafnium silicate thin films using liquid precursors and ozone," J. Vac. Sci. Technol. A 22(4), Jul./Aug. 2004.
Triyoso, D.H. et al. "Physical and electrical characteristics of $HfO_2$ gate dielectrics deposited by ALD and MOCVD," J. Electrochem. Soc., 152 (3) G203-G209 (2005).
Vollmerhaus, R. et al., "Synthesis and structure of Group 4 iminophosphonamide complexes," Organometallics, 2005, vol. 24, pp. 494-507.
Williams, P.A. et al., "Novel mononuclear alkoxide precursors for the MOCVD of ZrO2 and HfO2 thin films," Chem Vap. Deposition 2002, 8, No. 4, pp. 163-170.
Winter, C.H. et al., "Metallic materials deposition: metal-organic precursors," Encyclopedia of Inorganic Chemistry, 2006, John Wiley & Sons Ltd., DOI: 10.1002/ 0470862106.ia138.
International Search Report and Written Opinion for corresponding PCT/EP2007/052507, Oct. 31, 2007.
International Search Report and Written Opinion for related PCT/EP2006/062893, Sep. 27, 2007.
International Search Report and Written Opinion for related PCT/EP2009/051683, May 14, 2009.
Codato, S. et al. "MOCVD growth and characterization of $ZrO_2$ thin films obtained from unusual organo-zirconium precursors," Chemical Vapor Deposition, Wiley-VCH Verlag, Weinheim, Germany, vol. 11, No. 11, 1999, pp. 159-164.
Jutzi, P. et al., "Halbsandwich-Komplexe der Elemente Titan and Zirconium mit dem (Diisopropylaminoethyl) cyclopentadienyl-Ligand: Molekülstruktur von $[(C_5H_4CH_2CH_2N(H)^i Pr_2)ZrCl_3]^+Cl^-\cdot 2CH_3OH$", Journal of Organometallic Chemistyr 533 (1997), 237-245.
Niinisto, J.T., "Atomic layer deposition of high-$k$ dielectrics from novel cyclopentadienyl-type precursors," Dissertation, Helsinki University of Technology, Helsinki, Finland, Inorganic Chemistry Publication Series, Espoo 2006 No. 5, May 12, 2006.
Niinisto, J.T. et al., "Development of novel processes for atomic layer deposition of high-k dielectrics", $72^{nd}$ Annual Meeting of the DPG, Feb. 27, 2008, Berlin.
Niinisto, J.T. et al. "In situ quadrupole mass spectrometry study of atomic-layer deposition of $ZrO_2$ using $Cp_2Zr(CH_3)_2$ and water," Langmuir, 7321, 21, 2005.
Chen, P. et al., "Effect of nitrogen containing plasmas on interface stability of hafnium oxide ultrathin films on Si(100)," Applied Physics Letters, vol. 85, No. 9, Aug. 30, 2004, pp. 1574-1576.
Hausmann, D.M. et al., "Surface morphology and crystallinity control in the atomic layer deposition (ALD) of hafnium and zirconium oxide thin films," Journal of Crystal Growth 249 (2003), pp. 251-261.
Osipov, K.A. et al., "Use of ion beams and a high-frequency discharge for the precipitation of dielectric and metal films," Izvestiya Akademii Nauk SSSR, Neorganischeskie Materialy (1971) 7(6) pp. 1051-1052, English abstract only.
Pezzi, R.P. et al., "Hydrogen and deuterium incorporation and transport in hafnium-based dielectric films on silicon," Applied Physics Letters, vol. 85, No. 16, Oct. 18, 2004, pp. 3540-3542.
Qian, X. et al., Synthesis of new substituted cyclopentadienyl titanium monomethoxydifluorides with $BF_3\cdot OEt_2$ as fluorinating reagent and their use in syndiotactic polymerization of styrene, Journal of Organometallic Chemistry 689 (2004), pp. 1503-1510.
Zhu, J. et al., "Enhanced dielectric properties of $ZrO_2$ thin films prepared in nitrogen ambient by pulsed laser deposition," J. Phys. D: Appl. Phys. 36 (2003), pp. 389-393.
European Search Report for related EP 08305035.4, Jun. 13, 2008.
Request for Ex Parte Reexamination of related U.S. Pat. No. 8,668,957, filed Aug. 6, 2014.
Request for Ex Parte Reexamination of related U.S. Pat. No. 8,470,402, filed Aug. 6, 2014.
First Office Action for U.S. Appl. No. 90/013,315, Feb. 26, 2015.
First Office Action for U.S. Appl. No. 90/013,316, Feb. 26, 2015.
Niinisto, J., Atomic Layer Deposition of High-k Dielectrics from Novel Cyclopentadienyl-Type Precursors (May 12, 2006).
Second Office Action for U.S. Appl. No. 90/013,315, Jul. 16, 2015.
Second Office Action for U.S. Appl. No. 90/013,316, Jul. 15, 2015.

* cited by examiner

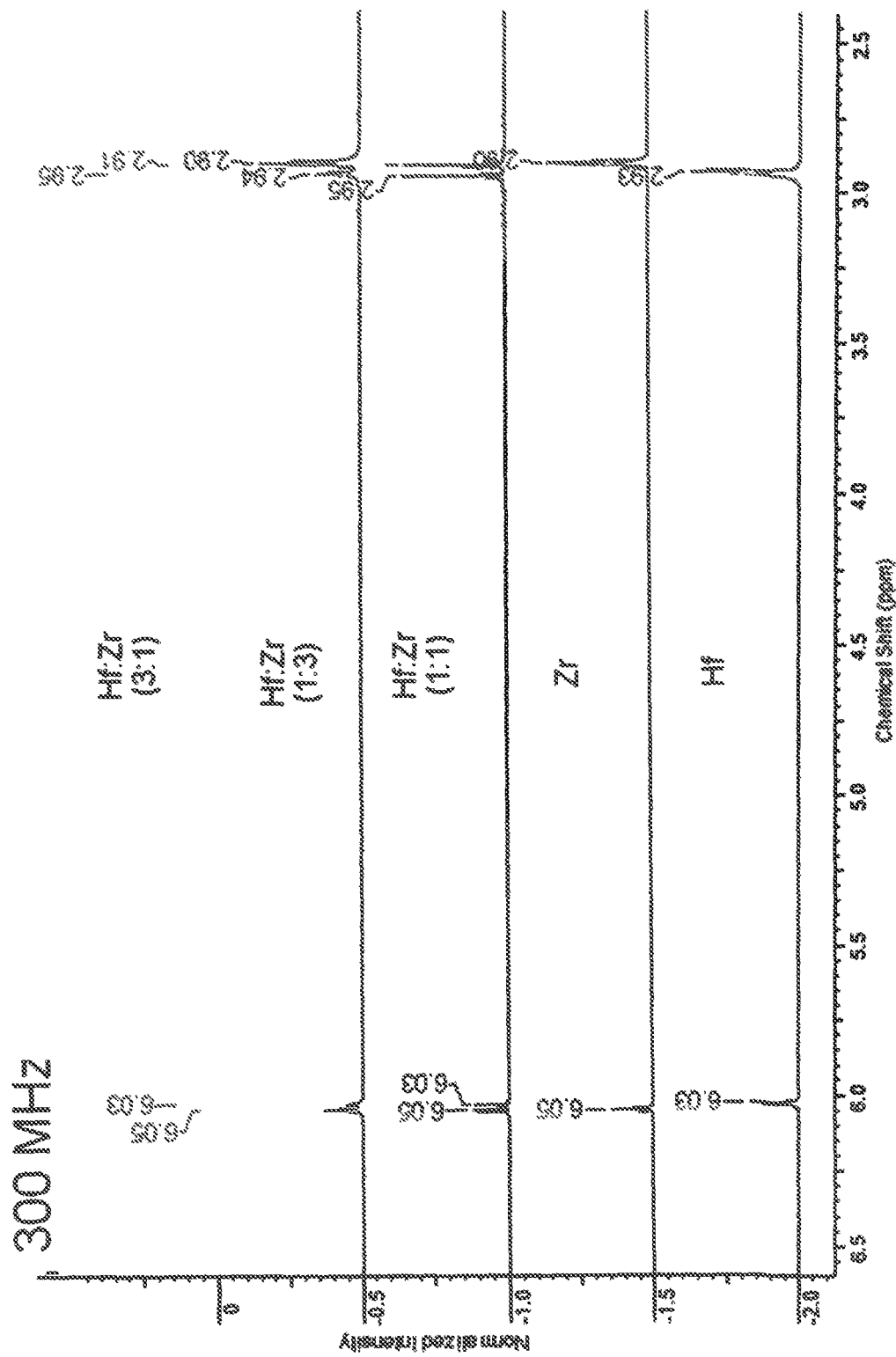

METHOD OF FORMING DIELECTRIC FILMS, NEW PRECURSORS AND THEIR USE IN SEMICONDUCTOR MANUFACTURING

CROSS REFERENCE TO RELATED APPLICATIONS

This application is a continuation-in-part of pending U.S. application Ser. No. 12/303,169 having a 371(c) filing date of Apr. 3, 2009, which is a national stage entry under 21 USC §371 of PCT/EP07/052,507 filed Mar. 16, 2007, which claims priority to PCT/EP06/062893 filed Jun. 2, 2006, the entire contents of each being incorporated herein by reference.

BACKGROUND

The invention relates to a method of forming high-k dielectric films such as hafnium or zirconium oxides or oxynitrides and their use for manufacturing semi-conductors.

With the shrink of the critical dimensions of the future generation of semi-conductor devices, the introduction of new materials, especially having high dielectric constant, is required. In CMOS architectures, high-k dielectrics are required to replace $SiO_2$ which reaches its physical limits, having typically a $SiO_2$ equivalent thickness of about 1 nm.

Similarly, high-k dielectrics are required in Metal-Insulator-Metal architectures for RAM applications. Various metal compositions have been considered to fulfill both the materials requirements (dielectric constant, leakage current, crystallization temperature, charge trapping) and the integration requirements (thermal stability at the interface, dry etching feasibility . . . ).

The Group IV based materials, such as $HfO_2$, $HfSiO_4$, $ZrO_2$, $ZrSiO_4$, $HfZrO_4$, $HfLnO_x$ (Ln being selected from the group comprising scandium, yttrium and rare-earth elements) and more generally HfMOx and ZrMOx, M being an element selected from Group II, Group IIIa and Group IIIb, or a transition metal, are among most promising materials. Furthermore, Group IV metals composition can also be considered for electrode and/or Cu diffusion barrier applications, such as TiN for mid-gap metal gate and HfN, ZrN, HfSi, ZrSi, HfSiN, ZrSiN, TiSiN for MIM electrodes.

The main industrial options to enable the deposition of such thin films with a reasonable throughput and an acceptable purity are vapor phase deposition techniques, such as MOCVD (Metal-Organic Chemical Vapor Deposition) or ALD (Atomic Layer Deposition). Such deposition processes require metal precursors that must fulfill drastic requirements for a proper industrial use. Metal-organic or metal-halide precursors are required for those processes. Various hafnium and zirconium metal-organic compounds have been considered as precursors to enable such a deposition.

Halides such as $HfCl_4$, $ZrCl_4$ are the most common Hf/Zr precursors and have been widely described. Kim et al. disclosed the use of $HfCl_4$ for the deposition of $HfO_2$ by ALD (Kim et al., Electrochem Soc Proceedings 2005-05, 397, 2005). However, some by-products generated during the deposition process, such as HCl or $Cl_2$, can cause surface/interface roughness that can be detrimental to the final properties. Other possible byproducts, depending on the oxygen source used, may be hazardous. For instance, $OCl_2$, through the OCl fragment by QMS, has been detected as a byproduct of the reaction between $HfCl_4$ and $O_3$. Moreover, in the case of high-k oxide, Cl or F impurities are highly detrimental to the final electrical properties.

Triyoso et al. and Chang et al. studied the use of $Hf(OtBu)_4$ for $HfO_2$ MOCVD and ALD, respectively [Triyoso et al.; J. Electrochem. Soc., 152(3), G203-G209 (2005); Chang et al.; Electrochem. Solid. State Let., 7(6), F42-F44 (2004)]. Williams et al. have evaluated $Hf(mmp)_4$ and $Hf(OtBu)_2(mmp)_2$ for MOCVD of $HfO_2$. In WO2003035926, Jones et al. disclose solid Ti, Hf, Zr and La precursors improved with donor functionalized alkoxy ligand (1-methoxy-2-methyl-2-propanolate $[OCMe_2CH_2OMe$, mmp]) which helps inhibiting oligomerization of Zr and Hf alkoxide compounds and increasing their stability towards moisture. However, all those alkoxide precursors have the drawback not to enable self-limited deposition in ALD process as suggested by Potter et al. (R. J. Potter, P. R. Chalker, T. D. Manning, H. C. Aspinall, Y. F. Loo, A. C. Jones, L. M. Smith, G. W. Critchlow, M. Schumacher, Chem. Vap. Deposition, 2005, 11, N° 3, 159-167).

Alkylamides precursors such as $Hf(NEtMe)_4$, $Hf(NMe_2)_4$, $Hf(NEt_2)_4$ have been widely disclosed in the literature [Senzaki et al, J. Vac. Sci. Technol. A 22(4) July/August 2004; Haussmann et al, Chem. Mater. 2002, 14, 4350-4353; Kawahara et al., J. Appl. Phys., Vol 43, N° 7A, 2004, pp 4129-4134; Hideaki et al., JP 2002-093804; Metzner et al. U.S. Pat. No. 6,858,547; Dip et al. US 2005/0056219 A1]. Group IV alkylamides are both suitable for ALD and MOCVD processes. Furthermore, some are liquid at room temperature ($Hf(NEt_2)_4$ and $Hf(NEtMe)_4$) and of sufficient volatility, and they allow self-limited ALD at low temperature for a limited thermal budget process. However, Group IV alkylamides, alkylamides in particular Zr compounds, have several drawbacks, among which they may decompose during the distribution to some extent leading to a possible clogging of the feeding line or the vaporizer, they may generate particles during deposition, they may entail non-uniform compositions during deep trenches deposition processes, and they only allow a narrow self-limited ALD temperature window, hence reducing the process window. In particular, $Zr(NEtMe)_4$ may decompose in the distribution lines and generate particles above 170° C. which is a common distribution temperature. $Hf(NEtMe)_4$ is more thermally stable yet do not afford self-limited atomic layer deposition above 300° C. due to thermal decomposition.

In WO 2007/055088, Thenappan et al. disclose hafnium and zirconium guanidinates complexes and their application for vapor phase deposition. $Hf(NEt_2)_2[(NiPr—CNEt_2]_2$ is given as example. Hafnium and zirconium guanidinates are however generally solids with a very limited volatility. As exemplified in thermal gravimetric analysis, one may not obtain $Hf(NEt_2)_2[(NiPr—CNEt_2]_2$ in vapour phase, without a risk of thermal decomposition and a subsequent particle generation.

Lehn et al. (Chem. Vap. Deposition, 2006, 12, 280-284) disclose tetrakis(trimethylhydrazido) zirconium [Zr(NMeNMe$_2$)$_4$,] and hafnium and their use for low temperature CVD. The exemplified compounds have an acceptable volatility (sublimation at 0.06 Torr, 90° C. reported) but they are solid at room temperature.

Carta et al. disclose the use of bis(cyclopentadienyl) bisdimethyl hafnium, $[HfCp_2Me_2]$ (Carta et al. discloses in Electrochem Soc Proceedings, 260, 2005-09, 2005) and several authors (Codato et al., Chem Vapor Deposition, 159, 5, 1995; Putkonen et al., J Mater Chem, 3141, 11, 2001; Niinisto et al., Langmuir, 7321, 21, 2005) proposed a new family of Zr and Hf compounds as alternatives to hafnium and zirconium alkylamides: Bis(cyclopentadienyl) bisdimethyl hafnium, bis(cyclopentadienyl) bisdimethyl zirconium, which allow an efficient ALD deposition process with an ALD window up to 400° C. and an achievement of films with less than 0.2% C in optimized conditions with $H_2O$ as co-reactant. However, $HfCp_2Me_2$ and $ZrCp_2Me_2$ both have the drawback of being solid products at room temperature ($HfCp_2Me_2$ melting point is 57.5° C.). This prevents IC makers to use those precursors in an industrial manner, that is using delocalized containers filling, and entail both facilitation and process issues.

In U.S. Pat. No. 6,743,473, Parkhe et al. disclose the use of $(Cp(R)_n)_xMH_{y-x}$, to make a metal and/or a metal nitride layer, where M is selected from tantalum, vanadium, niobium and hafnium, Cp is cyclopentadienyl, R is an organic group. Only examples of tantalum and niobium cyclopentadienyl compounds are disclosed. However, no liquid precursor or a precursor having a melting point lower than 50° C. is disclosed.

Liquid bis(cyclopentadienyl) derivatives have recently been proposed by Heys et al. in WO 2006/131751 A1. However, they still present the disadvantage of limited volatility and also present large steric hindrance that may limit the achieved growth rate.

Today, there is a need for providing liquid or low melting point (<50° C.) group IV precursor compounds, and in particular Hf and Zr compounds, that would allow simultaneously a proper distribution (physical state, thermal stability at distribution temperatures), a wide self-limited ALD window, and a deposition of pure films either by ALD or MOCVD.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein:

FIG. 9 is 300 MHz $^1H$ NMR spectra of the blends of $ZrCp(NMe_2)_3$ and $Hf(MeCp)(NMe_2)_3$ after 8 hours at 150° C.

DESCRIPTION OF PREFERRED EMBODIMENTS

Figure 1:
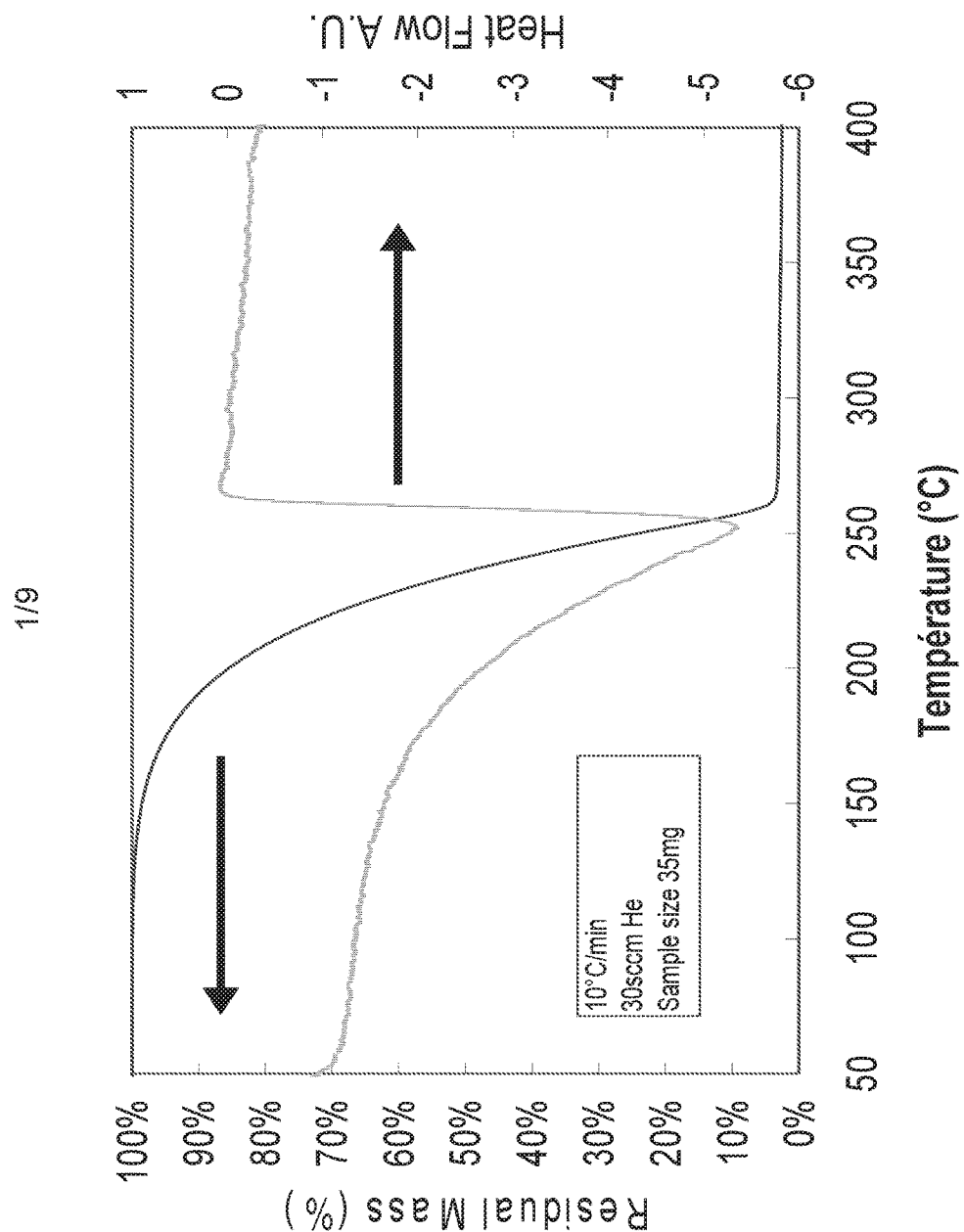
FIG. 1 is a Thermal Gravimetric Analysis (TGA) graph showing the percent residual mass versus temperature for (ethylcyclopentadienyl)tris(dimethylamino)zirconium [Zr(EtCp)(NMe₂)₃]

According to the invention, certain cyclopentadienyl or pentadienyl based group IV metal-organic precursors have been found suitable for the deposition of Group IV metal containing thin films by either ALD or MOCVD processes and to have the following advantages:

They are liquid at room temperature or having a melting point lower than 50° C., They are thermally stable to enable proper distribution (gas phase or direct liquid injection) without particles generation, They are thermally stable to allow wide self-limited ALD window, 4) allowing deposition of a variety of Group IV metals containing films, including ternary or quaternary materials, by using one or a combination of co-reactants (selected from the group comprising of $H_2$, $NH_3$, $O_2$, $H_2O$, $O_3$, $SiH_4$, $Si_2H_6$, $Si_3H_8$, TriDMAS, BDMAS, BDEAS, TDEAS, TDMAS, TEMAS, $(SiH_3)_3N$, $(SiH_3)_2O$, TMA or an aluminum-containing precursor, TBTDET, TAT-DMAE, PET, TBTDEN, PEN, lanthanide-containing precursors such as Ln(t-mhd)₃ . . . ).

According to a first embodiment, the invention relates to a method of deposition on a substrate, of at least one metal containing dielectric film comprising a compound of the formula (I):

$$(M^1_{1-a}M^2_a)O_bN_c,\qquad(I)$$

wherein:
0≤a<1,
0<b≤3, preferably 1.5≤b≤2.5;
0≤c≤1,
$M^1$ represents a metal selected from hafnium (Hf), zirconium (Zr) and titanium (Ti); and
$M^2$ represents a metal atom selected from magnesium (Mg), calcium (Ca), zinc (Zn), bore (B), aluminum (A), indium (In), silicon (Si), germanium (Ge), tin (Sn), hafnium (Hf), zirconium (Zr), titanium (Ti), vanadium (V), niobium (Nb), tantalum (Ta); and the Lanthanides atoms, more particularly scandium (Sc), yttrium (Y) and lanthanum (La) and rare-earth metal atoms, which comprises the following steps:

A step a) of providing a substrate into a reaction chamber;

A step (b) of vaporizing at least one $M^1$ metal containing precursor of the formula (II):

$$(R^1_yOp)_x(R^2_tCp)_zM^1R'_{4-x-z}\qquad(II)$$

wherein:
$M^1$ is as hereinabove defined;
0≤x≤3, preferably x=0 or 1;
0≤z≤3, preferably z=1 or 2;
1≤(x+z)≤4;
0≤y≤7, preferably y=2 0≤t≤5, preferably t=1;
($R^1_yOp$) represents a pentadienyl (Op) ligand, which is either unsubstituted or substituted by one ore more $R^1$ groups, y representing the number of substituting $R^1$ groups on said pentadienyl ligand;
($R^2_tCp$) represents a cyclopentadienyl (Cp) ligand, which is either unsubstituted or substituted by one or more $R^2$ groups, t representing the number of substituting $R^1$ groups on said cyclopentadienyl ligand;

R[1] and R[2], are identical or different and are independently selected from the group consisting of the chloro group, the linear or branched, alkyl groups having from one to four carbon atoms, the N-alkyl amino groups, wherein the alkyl group is linear or branched and has from one to four carbon atoms, the N,N-dialkyl amino groups, wherein each alkyl group, identical or different from the other, is linear or branched and has from one to four carbon atoms, the linear or branched alkoxy groups, having from one to four carbon atoms, the alkylsilylamides groups, the amidinates groups and the carbonyl group;

R' represents a ligand independently selected from the group consisting of the hydrogen, fluoro, chloro, bromo or iodo atoms, the linear or branched, alkyl groups having from one to four carbon atoms, the N-alkyl amino groups, wherein the alkyl group is linear or branched and has from one to four carbon atoms, the N,N-dialkyl amino groups, wherein each alkyl group, identical or different from the other, is linear or branched and has from one to four carbon atoms, the linear or branched alkoxy groups, having from one to four carbon atoms, the alkylsilyl amino groups wherein the alkyl group is linear or branched and has from one to four carbon atoms, the dialkylsilyl amino groups wherein each alkyl group, identical or different from the other, is linear or branched and has from one to four carbon atoms, the trialkylsilyl amino groups wherein each alkyl group, identical or different from the other, is linear or branched and has from one to four carbon atoms, the amidinates groups and the carbonyl, being understood that, if said formula (II) comprises more than one R' groups, each R' may be identical or different one from another, to form a first gas phase metal source;

Optionally a step b') of vaporizing at least one $M^2$ metal containing precursor, $M^2$ being as hereinabove defined; to form an optional second gas phase metal source;

A step c) of introducing said first gas phase metal source and said optional second gas phase metal source, in the reaction chamber, in order to provoke their contact with said substrate, to generate the deposition of a metal containing dielectric film comprising a compound of the formula (I) as hereinbefore defined, on said substrate;

provided that, if the at least one metal containing dielectric film to be formed comprises the compound of the formula (I'):

$$M^1{}_1O_2 \quad (I'),$$

corresponding to the formula (I), as hereinbefore defined wherein, a=0, b=2, and c=0, and if the $M^1$ metal containing precursor, which is involved in step b), is a compound of the formula (II'):

$$(R^2{}_tCp)_2M^1R'_2 \quad (II'),$$

corresponding to the formula (II) as hereinabove defined wherein x=0, and z=2, in said formula (II'), t>0 in at least one of the two ($R^2{}_tCp$) ligands.

In the method as hereinabove defined, the at least one metal containing precursor of the formula (II) and if necessary, the least one $M^2$ metal containing precursor, have a melting point generally below 50° C., preferably below 35° C. and they are preferably liquid at room temperature.

According to a particular embodiment of the method as hereinbefore defined, the vaporization step b) and if necessary, the vaporization step b') are achieved by introducing a carrier gas into a heated container containing the at least one $M^1$ metal containing precursor of the formula (II):

$$(R^1{}_yOp)_x(R^2{}_tCp)_zM^1R'_{4-x-z} \quad (II)$$

and if necessary, both the at least one $M^2$ metal containing precursor. The container is preferably heated at a temperature allowing to get the said metal sources in liquid phase and at a sufficient vapor pressure. If necessary, one or both metal precursors may be mixed to a solvent or to a mixture of solvents and/or to a stabilizer. The said solvent is for example selected from octane, hexane, pentane or tetramethylsilane. The concentration of the metal precursors in the solvent or in the mixture of solvents is usually between 0.01M and 0.5M and is more particularly around 0.05M. The carrier gas is selected, without limitation, from Ar, He, $H_2$, $N_2$ or mixtures of thereof.

If necessary, the container may be heated at temperatures in the range of 80-110° C. Those skilled in the art will consider that the temperature of the container can be adjusted to control the amount of precursor to be vaporized.

The carrier gas flow is usually comprised between 10 sccm (standard cubic centimeter) and 500 sccm. Preferably, the carrier gas flow is comprised between 50 sccm and 200 sccm.

According to another particular embodiment of the method as hereinbefore defined, the vaporization step b) and if necessary, the vaporization step b') are achieved by introducing in a liquid form, the $M^1$ metal containing precursor of the formula (II):

$$(R^1{}_yOp)_x(R^2{}_tCp)_zM^1R'_{4-x-z} \quad (II)$$

and if necessary both the $M^2$ metal containing precursor to a vaporizer where it is vaporized. If necessary, one or both metal precursors may be mixed to a solvent or to a mixture of solvents and/or to a stabilizer. The said solvent is for example selected from octane, hexane, pentane or tetramethylsilane. The concentration of the metal precursors in the solvent or in the mixture of solvents is usually between 0.01M and 0.5M and is more particularly around 0.05M.

According to a more particular embodiment, the vaporization step b) and the vaporization step b') are combined in one vaporization step b") of both sources.

During the step c) of the method as hereinbefore defined, the vaporized metal containing precursor is introduced into a reaction chamber where it is contacted to a substrate.

In the context of the present invention, substrate means any substrate used in the semiconductor, photovoltaic, LCD-TFT, or flat panel manufacturing, which, because of their technical function, requires to be coated by metal containing films. Such substrates are for example not only selected from silicon substrates (Si), silica substrates ($SiO_2$), silicon nitride substrates (SiN) or silicon oxy nitride substrates (SiON), but also from tungsten substrates (W) or noble metal substrates such as for example, Platinum substrates (Pt), Palladium substrates (Pd), Rhodium substrates (Rh) or gold substrates (Au). Plastic substrates, such as poly(3,4-ethylenedioxythiophene)poly (styrenesulfonte) [PEDOT:PSS], may also be used.

The substrate is heated until the required temperature to obtain the desired film with a sufficient growth rate and with the desired physical state and composition.

The temperature during step c), usually ranges from 150° C. to 600° C. Preferably the temperature is lower or equal to 450° C.

The pressure in the reaction chamber is controlled to obtain the desired metal containing film with a sufficient growth rate. The pressure during step c) usually ranges from around 1 mTorr (0.1333224 Pa) to around 100 Torr (13332.24 Pa).

In the context of the present invention, the M² metal containing precursor, is selected from the group consisting of:

Silicon derivatives or their Germanium homologues, such as:

disiloxane, trisilylamine, disilane, trisilane, alkoxysilane of the formula: (III₁)

$$SiH_x(OR^3)_{4-x}, \qquad (III_1)$$

wherein: 0≤x≤3 and R³ represents a linear or branched hydrocarbon group having 1 to 6 carbon atoms;
silanol derivative of the formula (III₂):

$$Si(OH)_x(OR^4)_{4-x} \qquad (III_2)$$

wherein: 1≤x≤3 and R⁴ represents a linear or branched alkyl group, having 1 to 6 carbon atoms, preferably Si(OH)(OR⁴)₃ and more preferably Si(OH)(OtBu)₃; aminosilane derivative of the formula (III₃):

$$SiH_x(NR^5R^6)_{4-x} \qquad (III_3)$$

wherein: 0≤x≤3 and R⁵ and R⁶ are identical or different and independently represents an hydrogen atom or a linear or branched alkyl having 1 to 6 carbon atoms, preferably SiH(NMe₂)₃ (TriDMAS); SiH₂(NHtBu)₂ (BTBAS); SiH₂(NEt₂)₂ (BDEAS)) and mixtures thereof;

Aluminum derivatives, such as trimethylaluminum [Al(CH₃)₃], dimethyl aluminum hydride [AlH(CH₃)₂], alkoxyalane of the formula (IV₁):

$$AlR^8_x(OR^7)_{3-x} \qquad (IV_1)$$

wherein: 0≤x≤3 and R⁷ represents a linear or branched alkyl having 1 to 6 carbon atom, and R⁸, identical to or different from R⁷, represents an hydrogen atom, or preferably AlR⁹R¹⁰(OR⁷), with R⁹ and R¹⁰ identical or different, which independently represent an linear or branched alkyl having 1 to 6 carbon atoms, most preferably AlMe₂(OiPr);

amidoalane of the formula (IV₂):

$$AlR^{11}_x(NR^{12}R^{13})_{3-x} \qquad (IV_2)$$

wherein: 0≤x≤3 and R¹² and R¹³ identical or different, represent an hydrogen atom or a linear or branched alkyl having 1 to 6 carbon atoms, and R¹¹, identical to or different from R⁷ and, represents an hydrogen atom or a linear or branched alkyl having 1 to 6 carbon atoms;

Tantalum derivatives, such as: Ta(OMe)₅, Ta(OEt)₅, Ta(NMe₂)₅, Ta(NEt₂)₅, Ta(NEt₂)₅, a tantalum derivative of the formula (V₁):

$$Ta(OR^{14})_4[O-C(R^{15})(R^{16})-CH_2-OR^{17}] \qquad (V_1)$$

wherein R¹⁴, R¹⁵, R¹⁶ and R¹⁷, identical or different, independently represent an hydrogen atom or a linear or branched alkyl having 1 to 6 carbon atoms, preferably Ta(OEt)₄(OCMe₂CH₂—OMe) (TAT-DMAE), a tantalum derivative of the formula (V₂):

$$Ta(OR^{18})_4[O-C(R^{19})(R^{20})-CH_2-N(R^{21})(R^{22})] \qquad (V_2)$$

wherein R¹⁸, R¹⁹, R²⁰, R²¹ and R²² identical or different, independently represent an hydrogen atom or a linear or branched alkyl having 1 to 6 carbon atoms, a tatalum derivative of the formula (V₃):

$$Ta(=NR^{24})(NR^{25}R^{26})_3 \qquad (V_3)$$

wherein R²⁴, R²⁵ and R²⁶, identical or different, independently represent an hydrogen atom or a linear or branched alkyl having 1 to 6 carbon atoms;

Niobium derivatives, such as Nb(OMe)₅, Nb(OEt)₅, Nb(NMe₂)₅, Nb(NEt₂)₄, Nb(NEt₂)₅, a niobium derivative of the formula (VI₁):

$$Nb(OR^{27})_4(O-C(R^{28})(R^{29})-CH_2-OR^{30}) \qquad (VI_1)$$

wherein R²⁷, R²⁸, R²⁹ and R³⁰, identical or different, independently represent an hydrogen atom or a linear or branched alkyl having 1 to 6 carbon atoms, preferably Nb(OEt)₄(OCMe₂CH₂—OMe) (NBT-DMAE), a niobium derivative of the formula (VI₂):

$$Nb(OR^{31})_4[O-C(R^{32})(R^{33})-CH_2-N(R^{34})(R^{35})] \qquad (VI_2)$$

wherein R³¹, R³², R³³, R³⁴ and R³⁵, identical or different, independently represent an hydrogen atom or a linear or branched alkyl having 1 to 6 carbon atoms, a niobium derivative of the formula (VI₃):

$$Nb(=NR^{36})(NR^{37}R^{38})_3 \qquad (VI_3)$$

wherein R³⁶, R³⁷ and R³⁸, identical or different, independently represent an hydrogen atom or a linear or branched alkyl having 1 to 6 carbon atoms;

lanthanide derivatives, such as scandium derivatives, yttrium derivatives, cerium derivatives, praseodinum derivatives, gadolinium derivatives, dysprosium derivatives, erbium derivatives, lanthanum derivatives, a derivative with at least one β-diketonate ligand or at least a cyclopentadienyl ligand optionally substituted with one or several linear or branched alkyl groups having 1 to 6 carbon atoms;

divalent metal derivatives, such as strontium (Sr), barium (Ba), magnesium (Mg), calcium (Ca) or zinc (Zn) derivatives, with at least one β-diketonate ligand or at least a cyclopentadienyl ligand optionally substituted with one or several linear or branched alkyl groups having 1 to 6 carbon atoms;

other metal derivatives such as tungsten (W), molybdenum (Mo), hafnium (Hf) or zirconium (Zr) derivatives, for example the alkoxy derivatives, the amino derivatives or adducts containing these species, being understood that said derivatives are not compounds of the formula (II) as hereinbefore defined.

According to another particular embodiment, the method as hereinbefore defined, comprise:

A step d), wherein the at least one M¹ metal containing precursor of the formula (II), and if necessary, the at least one M² metal containing precursor, is mixed to at least one reactant species prior to step c).

In the context of the invention, the at least one reactant species is chosen in relation to the targeted metal based film, which is expected According to another embodiment, the reactant species is an oxygen source and more particularly oxygen (O₂), oxygen containing radicals O. or OH., for instance generated by a remote plasma, ozone (O₃), moisture (H₂O) and H₂O₂ and mixture thereof.

According to another embodiment, the reactant species is a nitrogen source and more particularly nitrogen (N₂), nitrogen-containing radicals such as N., NH., NH₂., ammonia (NH₃), hydrazine (NH₂NH₂) and its alkyl or aryl derivatives, and mixtures thereof.

According to another embodiment, the reactant species is both a nitrogen and an oxygen source and more particularly, NO, NO₂, N₂O, N₂O₅, N₂O₄ and mixtures thereof.

Depending on the ratio N/O, which is required, the reactant species which is, if necessary, used in the method as hereinbefore defined, may be either an oxygen source, either a mixture of an oxygen source and of a nitrogen source, either both an oxygen and a nitrogen source, or a mixture thereof.

According to another embodiment of the invention, if the targeted metal based film contains carbon, such as for example without limitation metal carbide or metal carbonitride, at least one reactant species is a carbon source more particularly, methane, ethane, propane, butane, ethylene, propylene, t-butylene.

According to another embodiment of the invention if the targeted metal based film contains silicon, such as for example without limitation metal silicide, silico-nitride, silicate or silico-carbo-nitride, at least on reactant species is a silicon source such as:

disiloxane, trisilylamine, disilane ($Si_2H_6$), trisilane ($Si_3H_8$), alkoxysilane of the formulas ($III_1$), ($III_2$) or ($III_3$), as hereinbefore defined, for example $SiH(NMe_2)_3$ (TriDMAS); $SiH_2(NHtBu)_2$ (BTBAS); $SiH_2(NEt_2)_2$ (BDEAS)) and mixtures thereof.

According to another particular embodiment, the method as hereinbefore defined, comprise:

a step d') wherein the at least one $M^1$ metal containing precursor of the formula (II) and if necessary, the at least one $M^2$ metal containing precursor, is mixed to at least one reactant species in the reaction chamber.

The mode of introduction of the at least one $M^1$ metal containing precursor of the formula (II) and if necessary, the at least one $M^2$ metal containing precursor, and the at least one reactant species in the reaction chamber generally depends on the mode of deposition of the film on the substrate. The metal containing precursors and the reactant species are generally introduced simultaneously in a chemical vapor deposition process, or sequentially in an atomic layer deposition process or according to several combinations, as for example in a pulsed modified atomic layer deposition process wherein the at least one $M^1$ metal containing precursor of the formula (II) and if necessary, the at least one $M^2$ metal containing precursor, are introduced together in one pulse and the at least one reactant species is introduced in a separate pulse; or in a pulsed chemical vapor deposition process wherein the at least one $M^1$ metal containing precursor of the formula (II) and if necessary, the at least one $M^2$ metal containing precursor, are introduced by pulse and the at least one reactant species is introduced continuously.

According to another of the invention, the at least one reactant species is passed through a plasma system localized remotely from the reaction chamber, and decomposed to radicals.

According to another embodiment, the step (b) of the method as hereinabove defined, consists of a step ($b_1$) of mixing at least one first metal containing precursor of the formula (II) together with at least a second of the following precursors: $M^1(NMe_2)_4$, $M^1(NEt_2)_4$, $M^1(NMeEt)_4$, $M^1(mmp)_4$, $M^1(OtBu)_4$, $M^1(OtBu)_2(mmp)_2$ and mixtures thereof and a step ($b_2$) of vaporizing said mixture. According to a more particular embodiment, the invention concerns a method as hereinbefore defined, of deposition of a metal containing dielectric film comprising a compound of the formula (I), wherein the $M^1$ metal containing precursor is of the formula ($II_1$):

$$(R^2_xCp)M^1[N(R^{39})(R^{40})]_3 \quad (II_1)$$

corresponding to the formula (II), wherein x=0, z=1 and R' represents the group $N(R^{39})(R^{40})$, wherein $R^{39}$ and $R^{40}$, identical or different, independently represent an hydrogen atom, a linear or branched alkyl group having from one to four carbon atoms, an alkylsilyl group, wherein the alkyl group is linear or branched and has from one to four carbon atoms, a dialkylsilyl group, wherein each alkyl group, identical or different from the other, is linear or branched and has from one to four carbon atoms or a trialkylsilyl group wherein each alkyl group, identical or different from the other, is linear or branched and has from one to four carbon atoms According to a more particular embodiment, the invention concerns a method as hereinbefore defined, of deposition of a metal containing dielectric film comprising a compound of the formula ($I_1$):

$$M^1O_2 \quad (I_1)$$

corresponding to the formula (I), wherein a=0, b=2 and c=0, wherein the metal containing precursor of the formula (II) is selected from the group consisting of: $HfCp_2Cl_2$, $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(EtCp)_2Me_2$, $Hf(MeCp)_2(CO)_2$, $ZrCp_2Cl_2$, $Zr(MeCp)_2Me_2$, $ZrCp(MeCp)Cl_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$, $Zr(MeCp)(NMe_2)_3$, $Zr(EtCp)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)(NEt_2)_3$, $Zr(EtCp)(NEt_2)_3$, $ZrCp(NEt_2)_3$, $Zr(iPr_2Cp)(NMe_2)_3$, $Zr(tBu_2Cp)(NMe_2)_3$, $Hf(MeCp)(NMe_2)_3$, $Hf(EtCp)(NMe_2)_3$, $HfCp(NMe_2)_3$, $Hf(MeCp)(NEtMe)_3$, $Hf(EtCp)(NEtMe)_3$, $HfCp(NEtMe)_3$, $Hf(MeCp)(NEt_2)_3$, $Hf(EtCp)(NEt_2)_3$, $HfCp(NEt_2)_3$, $Hf(iPr_2Cp)(NMe_2)_3$, $Hf(tBu_2Cp)(NMe_2)_3$ and mixtures thereof.

According to a more particular embodiment, the invention concerns a method as hereinbefore defined, of deposition of a metal containing dielectric film comprising a compound of the formula ($I_2$):

$$M^1O_bN_c \quad (I_2)$$

corresponding to the formula (I), wherein a=0, 1.5≤b≤2.5 and 0<c≤0.5, wherein the metal containing precursor of the formula (II) is selected from the group consisting of: $HfCp_2Cl_2$, $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(EtCp)_2Me_2$, $Hf(MeCp)_2(CO)_2$, $ZrCp_2Cl_2$, $Zr(MeCp)_2Me_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$, $Zr(MeCp)(NMe_2)_3$, $Zr(EtCp)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)(NEt_2)_3$, $Zr(EtCp)(NEt_2)_3$, $ZrCp(NEt_2)_3$, $Zr(iPr_2Cp)(NMe_2)_3$, $Zr(tBu_2Cp)(NMe_2)_3$, $Hf(MeCp)(NMe_2)_3$, $Hf(EtCp)(NMe_2)_3$, $HfCp(NMe_2)_3$, $Hf(MeCp)(NEtMe)_3$, $Hf(EtCp)(NEtMe)_3$, $HfCp(NEtMe)_3$, $Hf(MeCp)(NEt_2)_3$, $Hf(EtCp)(NEt_2)_3$, $HfCp(NEt_2)_3$, $Hf(iPr_2Cp)(NMe_2)_3$, $Hf(tBu_2Cp)(NMe_2)_3$ and mixture thereof.

According to a more particular embodiment, the invention concerns a method as hereinbefore defined, of deposition of a metal containing dielectric film comprising a compound of the formula ($I_3$):

$$(M^1_{1-a}M^2_a)O_b \quad (I_3)$$

corresponding to the formula (I), wherein 0≤a<1 and c=0, wherein the metal containing precursor of the formula (II) is selected from the group consisting of: $HfCp_2Cl_2$, $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(EtCp)_2Me_2$, $Hf(MeCp)_2(CO)_2$, $ZrCp_2Cl_2$, $Zr(MeCp)_2Me_2$, $ZrCp(MeCp)Cl_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$, $Zr(MeCp)(NMe_2)_3$, $Zr(EtCp)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)(NEt_2)_3$, $Zr(EtCp)(NEt_2)_3$, $ZrCp(NEt_2)_3$, $Zr(iPr_2Cp)(NMe_2)_3$, $Zr(tBu_2Cp)(NMe_2)_3$, $Hf(MeCp)(NMe_2)_3$, $Hf(EtCp)$ (NMe$_2$)$_3$, HfCp(NMe$_2$)$_3$, Hf(MeCp)(NEtMe)$_3$, Hf(EtCp)(NEtMe)$_3$, HfCp(NEtMe)$_3$, Hf(MeCp)(NEt$_2$)$_3$, Hf(EtCp)(NEt$_2$)$_3$, HfCp(NEt$_2$)$_3$, Hf(iPr$_2$Cp)(NMe$_2$)$_3$, Hf(tBu$_2$Cp)(NMe$_2$)$_3$ and the M$^2$ metal containing precursor is preferably selected from the silicon derivatives or their germanium homologues, the tantalum derivatives, lanthanide derivatives, and the magnesium derivatives as hereinabove defined.

According to a more particular embodiment, the invention concerns a method as hereinbefore defined, of deposition of a metal containing dielectric film comprising a compound of the formula (I$_4$):

corresponding to the formula (I), wherein 0≤a<1 and 0<c≤0.5, wherein the metal containing precursor of the formula (II) is selected from the group consisting of HfCp$_2$Cl$_2$, Hf(MeCp)$_2$Me$_2$, HfCp(MeCp)Cl$_2$, Hf(MeCp)$_2$Cl$_2$, HfCp(MeCp)Me$_2$, Hf(EtCp)(MeCp)Me$_2$, Hf(EtCp)$_2$Me$_2$, Hf(MeCp)$_2$(CO)$_2$, ZrCp$_2$Cl$_2$, Zr(MeCp)$_2$Me$_2$, ZrCp(MeCp)Cl$_2$, Zr(MeCp)$_2$Cl$_2$, ZrCp(MeCp)Me$_2$, Zr(EtCp)(MeCp)Me$_2$, Zr(EtCp)$_2$Me$_2$, Zr(MeCp)$_2$(CO)$_2$, Zr(MeCp)(NMe$_2$)$_3$, Zr(EtCp)(NMe$_2$)$_3$, ZrCp(NMe$_2$)$_3$, Zr(MeCp)(NEtMe)$_3$, Zr(EtCp)(NEtMe)$_3$, ZrCp(NEtMe)$_3$, Zr(MeCp)(NEt$_2$)$_3$, Zr(EtCp)(NEt$_2$)$_3$, ZrCp(NEt$_2$)$_3$, Zr(iPr$_2$Cp)(NMe$_2$)$_3$, Zr(tBu$_2$Cp)(NMe$_2$)$_3$, Hf(MeCp)(NMe$_2$)$_3$, Hf(EtCp)(NMe$_2$)$_3$, HfCp(NMe$_2$)$_3$, Hf(MeCp)(NEtMe)$_3$, Hf(EtCp)(NEtMe)$_3$, HfCp(NEtMe)$_3$, Hf(MeCp)(NEt$_2$)$_3$, Hf(EtCp)(NEt$_2$)$_3$, HfCp(NEt$_2$)$_3$, Hf(iPr$_2$Cp)(NMe$_2$)$_3$, Hf(tBu$_2$Cp)(NMe$_2$)$_3$, the M$^2$ metal containing precursor is preferably selected from the silicon derivatives or their germanium homologues, the tantalum derivatives, lanthanide derivatives, and the magnesium derivatives as hereabove defined, and at least one oxygen containing precursor and at least one nitrogen containing precursor is introduced into the reactor.

According to another embodiment the invention concerns the use of the compounds of the formula (II) as hereinbefore defined, to make dielectric films more particularly for integrated circuits or in the preparation of Metal Insulator Metal (MIM) architectures for Random Access Memories.

According to another embodiment, the invention concerns a compound the formula (II$_1$):

corresponding to the formula (II), wherein x=0, z=1 and R' represents the group N(R$^{39}$)(R$^{40}$), wherein R$^{39}$ and R$^{40}$, identical or different, independently represent an hydrogen atom, a linear or branched alkyl group having from one to four carbon atoms, an alkylsilyl group, wherein the alkyl group is linear or branched and has from one to four carbon atoms, a dialkylsilyl group, wherein each alkyl group, identical or different from the other, is linear or branched and has from one to four carbon atoms or a trialkylsilyl group wherein each alkyl group, identical or different from the other, is linear or branched and has from one to four carbon atoms.

According to a particular embodiment, the invention relates to a compound of the formula (II$_1$) as hereinbefore defined, wherein R$^2$, R$^{39}$ and R$^{40}$, identical or different, independently represent a radical selected from the methyl, ethyl, propyl, isopropyl, butyl, isobutyl, sec-butyl and tert-butyl groups, and more specifically the following compounds:
Zr(MeCp)(NMe$_2$)$_3$, Zr(EtCp)(NMe$_2$)$_3$, ZrCp(NMe$_2$)$_3$, Zr(MeCp)(NEtMe)$_3$, Zr(EtCp)(NEtMe)$_3$, ZrCp(NEtMe)$_3$, Zr(MeCp)(NEt$_2$)$_3$, Zr(EtCp)(NEt$_2$)$_3$, ZrCp(NEt$_2$)$_3$, Zr(iPr$_2$Cp)(NMe$_2$)$_3$, Zr(tBu$_2$Cp)(NMe$_2$)$_3$, Hf(MeCp)(NMe$_2$)$_3$, Hf(EtCp)(NMe$_2$)$_3$, HfCp(NMe$_2$)$_3$, Hf(MeCp)(NEtMe)$_3$, Hf(EtCp)(NEtMe)$_3$, HfCp(NEtMe)$_3$, Hf(MeCp)(NEt$_2$)$_3$, Hf(EtCp)(NEt$_2$)$_3$, HfCp(NEt$_2$)$_3$, Hf(iPr$_2$Cp)(NMe$_2$)$_3$, Hf(tBu$_2$Cp)(NMe$_2$)$_3$, and mixtures thereof.

According to a more specific embodiment, the invention relates to the following compounds:
Zr(EtCp)(NMe$_2$)$_3$, Zr(MeCp)(NMe$_2$)$_3$, ZrCp(NMe$_2$)$_3$, Hf(EtCp)(NMe$_2$)$_3$, Hf(MeCp)(NMe$_2$)$_3$ and HfCp(NMe$_2$)$_3$, and mixtures thereof.

Those skilled in the art will recognize that the hereinabove metal-organic compounds could be used for any other applications than vapour phase deposition processes, such as catalysts or any other industrial process or application requiring the use of metal-organic compounds . . . .

According to another embodiment, the invention concerns a process for the preparation of a compound of the formula (II$_1$) as hereinabove defined, which comprises:
 a step 1, consisting of the preparation of the compound of the formula (VII$_1$):

wherein M$^1$, R$^2$ and t are as hereinabove defined for the formula (II), by the reaction of M$^1$Cl$_4$ with (R$^2_t$Cp)Na;
 a step 2, consisting of the reaction of the compound of the formula (VII$_1$) prepared in step 1, with NH(R$^{39}$)(R$^{40}$), to produce the compound of the formula (II$_1$).

According to a last embodiment, the invention concerns the following compounds of the formula (II) as hereinabove defined:
Hf(EtCp)$_2$Me$_2$, Zr(MeCp)$_2$Me$_2$ or Zr(EtCp)$_2$Me$_2$.

The following examples are an illustration of the various embodiments of the present invention, without being a limitation.

Example I

Deposition of Metal Oxide Film M$^1$O$_2$ with M$^1$ being Preferably Hafnium and Zirconium The film to be deposited comprises a compound of the formula (I) wherein a=0, b=2 and c=0.

To make the deposition of such film on the surface of a wafer or in a deep trench to manufacture MIM structures for DRAM, one need to vaporize the M$^1$ metal source as defined in step (b) and to introduce it into the reactor (preferably Hafnium or Zirconium), to inject an oxygen source, preferably moisture, oxygen or ozone into said reactor, react the products at appropriate temperature (preferably between 150° C. and 350° C.) and pressure (preferably between 25 Pa and 1000 Pa) for the duration necessary to achieve either a thin film deposition on the substrate or to fill out deep trenches by ALD or pulse CVD process (sequential pulse injection of metal sources are necessary in order to allow regular deposition of the oxide in the trench to progressively fill out this trench and provide no voids in the dielectric film and therefore no defect in the capacitor dielectric film).

The dielectric film shall have the desired final composition (here essentially variations of the b value around 2 modifying the ratio of precursor to oxygen source).

Three examples of types of compounds of the formula (II) were chosen according to the three following options a, b or c:
 a) The compound of the formula (II) is chosen from Zr(MeCp)$_2$Me$_2$, Zr(EtCp)$_2$Me$_2$, Hf(MeCp)$_2$Me$_2$ and Hf(MeCp)$_2$Me$_2$, and mixtures thereof.

Delivery of molecules in liquid form is usually carried out by bubbling an inert gas ($N_2$, He, Ar, . . . ) into the liquid and providing the inert gas plus liquid gas mixture to the reactor.

b) The compound of the formula (II) is chosen from $Zr(2,4-Me_2Op)_2Me_2$ and $Hf(2,4-Me_2Op)_2Me_2$.

c) The compound of the formula (II) is chosen from $Zr(MeCp)(2,4-Me_2Op)Me_2$ and $Hf(MeCp)(2,4-Me_2Op)Me_2$.

The oxygen source shall be preferably, without limitations, oxygen ($O_2$), oxygen radicals (for instance O or OH), such as radicals generated by a remote plasma system, ozone, NO, $N_2O$, $NO_2$, moisture ($H_2O$) and $H_2O_2$.

Regarding the deposition process by itself, the reactants can be introduced into the reactor simultaneously (chemical vapor deposition), sequentially (atomic layer deposition) or different combinations (one example is to introduce metal source and the other metal source together in one pulse and oxygen in a separate pulse [modified atomic layer deposition]; another option is to introduce oxygen continuously and/or to introduce the metal source by pulse (pulsed-chemical vapor deposition).

Example II

Deposition of Metal Oxynitride Films NOON with $M^1$ being Preferably Hafnium and Zirconium The film to be deposited comprises a compound of the formula (I) wherein a=0 and b and c are different from zero.

All the information given in Example I, is applicable in this Example II, except that nitrogen needs to be introduced into the reactor.

The nitrogen shall be selected from a nitrogen source selected from the group comprising nitrogen ($N_2$), ammonia, hydrazine and alkyl derivatives, N-containing radicals (for instance N., NH., $NH_2$.), NO, $N_2O$, $NO_2$ or the like.

Example III

Deposition of $M^1M^2$ Metal Oxide Films with $M^1$ being Preferably Hf or Zr and $M^2$ being Preferably Si or Al The film to be deposited comprises a compound of the formula (I) wherein a≠0, b≠0 and c=0.

All the information given in Example I is applicable in this Example III, except that a $M^2$ metal source is additionally needed.

The $M^2$ containing precursor is also introduced into the reactor to create the $M^2$ source of metal. This $M^2$ containing precursor source shall be preferably:

a) a silicon (or germanium) source, for example $Si(OH)(OtBu)_3$, $SiH(NMe_2)_3$ (TriDMAS); $SiH_2(NHtBu)_2$ (BTBAS) and $SiH_2(NEt_2)_2$ (BDEAS)

b) an aluminum source, for example $AlMe_2(OiPr)$; or c) a tantalum (or niobium) source, for example $Ta(OMe)_5$, $Ta(OEt)_5$ and $Ta(OEt)(OCMe_2CH_2—OMe)$ (TATDMAE);

The invention is directed to the deposition of dielectric films of the formula I, onto a support such as a wafer, in a reactor using ALD, CVD, MOCVD, pulse CVD processes.

Example IV

Deposition of $M^1M^2$ Metal Oxynitride Films with $M^1$ being Preferably Hf or Zr and $M^2$ being Preferably Si or Al The film to be deposited comprises a compound of the formula (I) wherein a≠0 b≠0 and c≠0.

All the information given in Example III, is applicable in this case, except that nitrogen needs to be introduced into the reactor.

The nitrogen source shall be selected from the group comprising nitrogen (N2), ammonia, hydrazine and alkyl derivatives, N-containing radicals (for instance N., NH., $NH_2$.), NO, $N_2O$, $NO_2$.

Example V

Synthesis of (Ethylcyclopentadienyl) Tris(Dimethylamino) Zirconium, $Zr(EtCp)(NMe_2)_3$ $Zr(EtCp)(NMe_2)_3$ is prepared in 3 steps.

The first step is the preparation of $Zr(EtCp)Cl_3$ by the reaction of (EtCp)Na over $ZrCl_4$;

The second step is the reaction $LiNMe_2$ with $Zr(EtCp)Cl_3$ to produce $Zr(EtCp)(NMe_2)_3$. The resulting compound is purified by distillation. Overall yield was 35%.

(Ethylcyclopentadienyl)tris(dimethylamino)zirconium has been found to be a stable liquid pale yellow compound.

TGA analysis of $Zr(EtCp)(NMe_2)_3$

The thermal gravimetric apparatus was stored in an argon glove box with moisture and oxygen content maintained below 1 ppmv. Thermal gravimetric analysis was performed by placing a 35 mg sample in an aluminum crucible. The sample was then heated at a 10° C./min temperature ramp from 35° C. to 400° C. The mass loss was monitored as a function of the crucible temperature. The residue level was 2.6% with full evaporation temperatures of 260° C. The resulting graph is on FIG. 1.

Example VI

Atomic Layer Deposition of $ZrO_2$ Thin Films Using $Zr(EtCp)(NMe_2)_3$ $Zr(EtCp)(NMe_2)_3$ is stored into a container. The container is heated at 90° C. and $N_2$ is used as carrier gas at a flow of 50 sccm. The pressure the container is controlled at 50 Torr. $O_3$ is used as oxygen source. The substrate is heated at 350° C. During a first step, $Zr(EtCp)(NMe_2)_3$ is introduced into the reaction chamber during 2s. A $N_2$ purge of 5s is performed afterwards as second step. As third step, a pulse of $O_3$ is then introduced into the reaction chamber during 2s, followed by a 2 s $N_2$ purge as fourth step. All four steps are repeated 100 times to obtain a $ZrO_2$ film. Self-limited atomic layer deposition is obtained.

Similar experiments can be performed with Hf analogs. Similar experiments can be conducted with $H_2O$ as oxygen source.

Example VII

Metal-Organic Chemical Vapor Deposition of $ZrO_2$ Using $Zr(EtCp)(NMe_2)_3$ $Zr(EtCp)(NMe_2)_3$ is stored into a container. The container is heated at 90° C. and $N_2$ is used as carrier gas at a flow of 50 sccm. The pressure in the container is controlled at 50 Torr. Zr(EtCp)(NMe$_2$)$_3$ is mixed to an O$_2$/N$_2$ gas mixture into the reaction chamber. The substrate is heated at 500° C. The pressure inside the reaction chamber is set at 10 Torr. A film of zirconium oxide is obtained.

Similar experiments can be performed with Hf analogs.

Example VIII

Comparison of Zr(EtCp)(NMe$_2$)$_3$ and Zr(NEtMe)$_4$ Thermal Behavior

Figure 2:
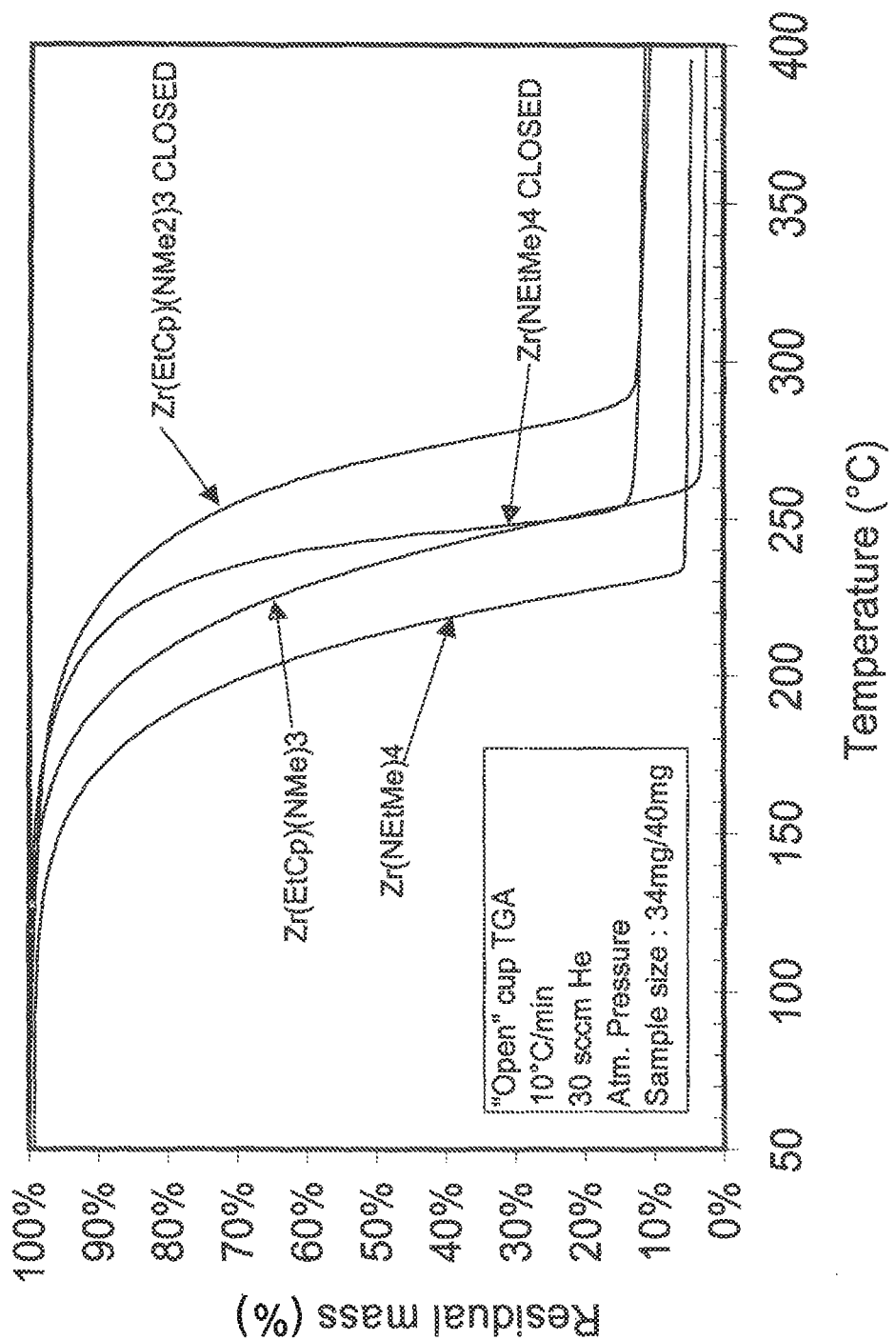
FIG. 2 is a TGA graph showing the percent residual mass versus temperature in open cup and closed cup configuration for $Zr(EtCp)(NMe_2)_3$ and tetrakis(ethylmethylamino)zirconium $[Zr(NEtMe)_4]$.

Thermal gravimetric analysis is performed on Zr(EtCp) (NMe$_2$)$_3$ and Zr(NEtMe)$_4$ in similar conditions. Thermal gravimetric apparatus was stored in an argon glove box with moisture and oxygen content maintained below 1 ppmv. Thermal gravimetric analysis was performed by placing a 35 mg sample in an aluminum crucible. The sample was then heated at a 10° C./min temperature ramp from 35° C. to 400° C. The mass loss was monitored as a function of the crucible temperature. In closed cup configuration, a pierced pan (0.8 mm) is placed over the crucible containing the metal-organic compound to slow down the evaporation. This indicates the thermal stability at higher temperature. The results indicates that Zr(EtCp)(NMe$_2$)$_3$ is much more thermally stable than Zr(NEtMe)$_4$, making it further attractive for use as vapor phase precursor. The results are shown on FIG. 2.

Example IX

Blends of ZrCp(NMe$_2$)$_3$ and HfCp(NMe$_2$)$_3$

Figure 3:
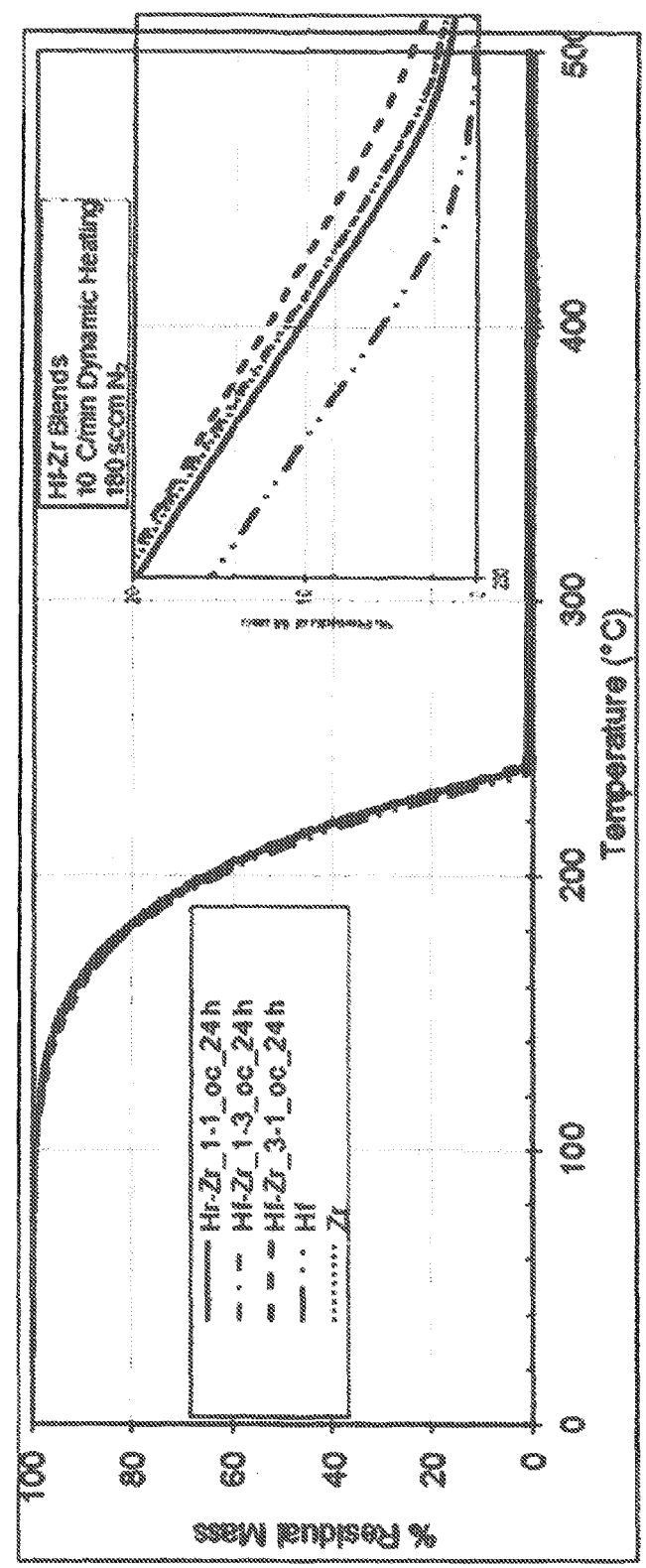
FIG. 3 is a TGA graph showing the percent residual mass versus temperature in open cup configuration for blends of $ZrCp(NMe_2)_3$ and $Hf(MeCp)(NMe_2)_3$.
Figure 4:
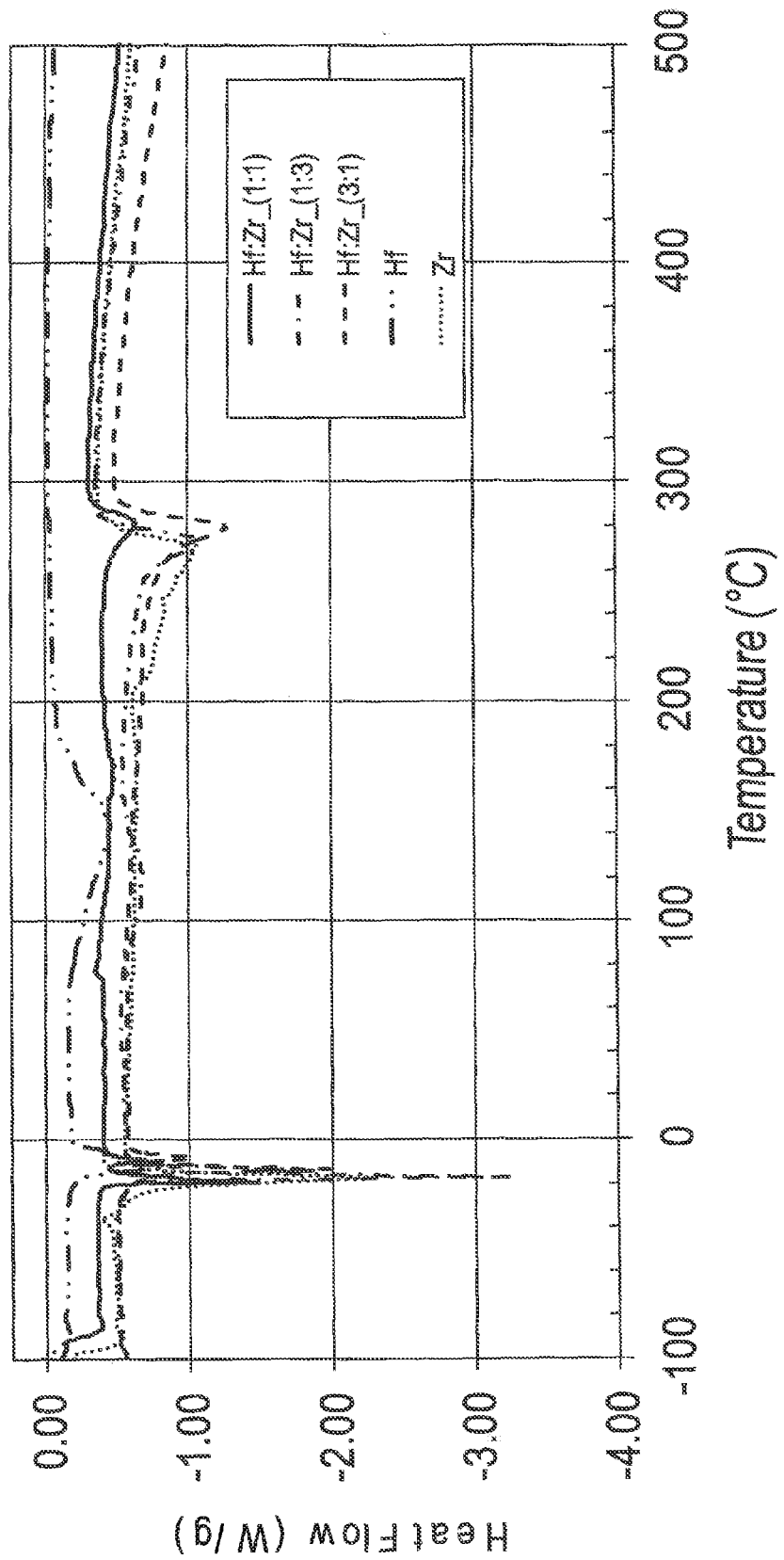
FIG. 4 is a Differential Scanning calorimetry graph showing the phase transitions for blends of $ZrCp(NMe_2)_3$ and $Hf(MeCp)(NMe_2)_3$.
Figure 5:
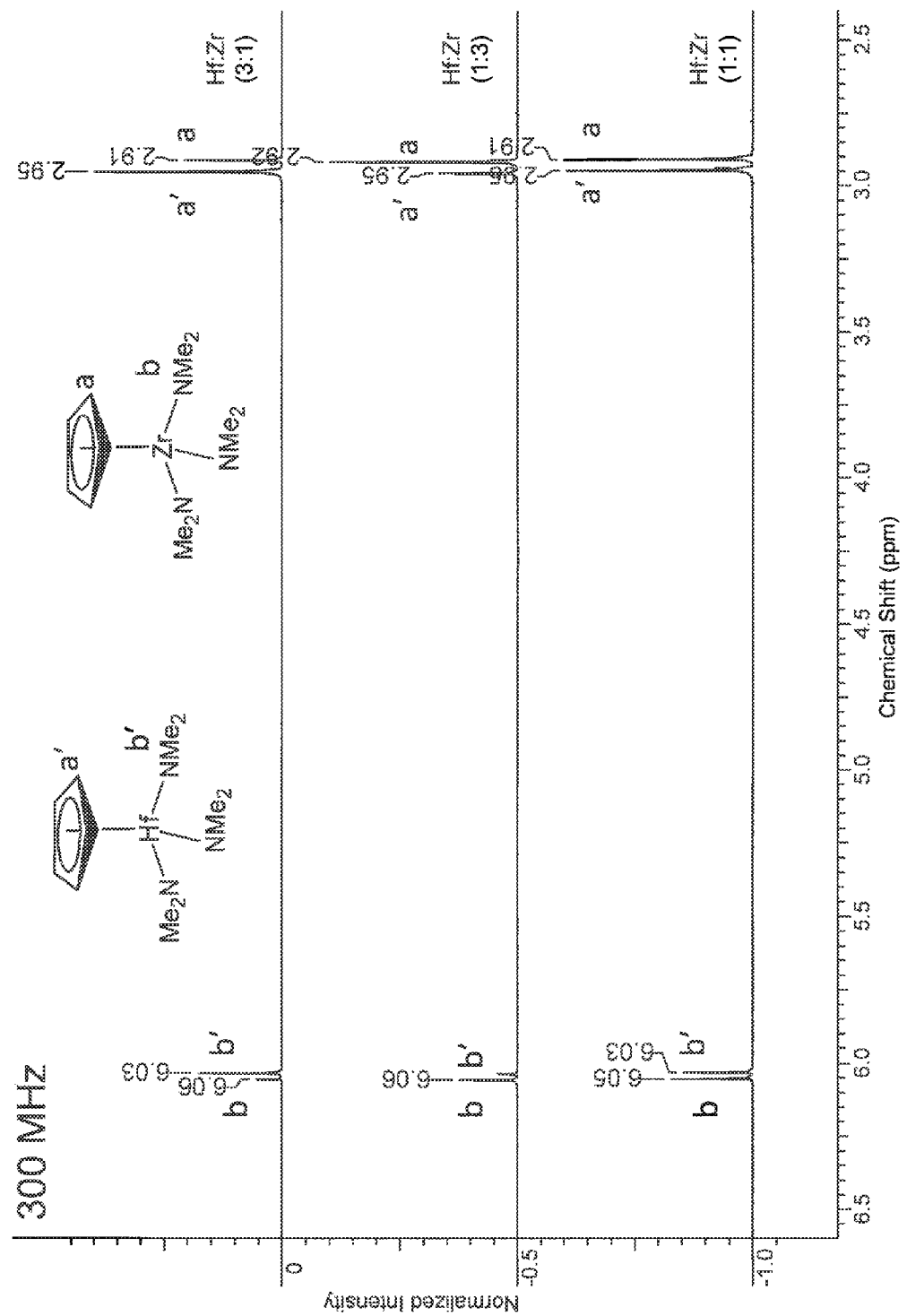
FIG. 5 is 300 MHz $^1H$ NMR spectra of the blends of $ZrCp(NMe_2)_3$ and $Hf(MeCp)(NMe_2)_3$.
Figure 6:
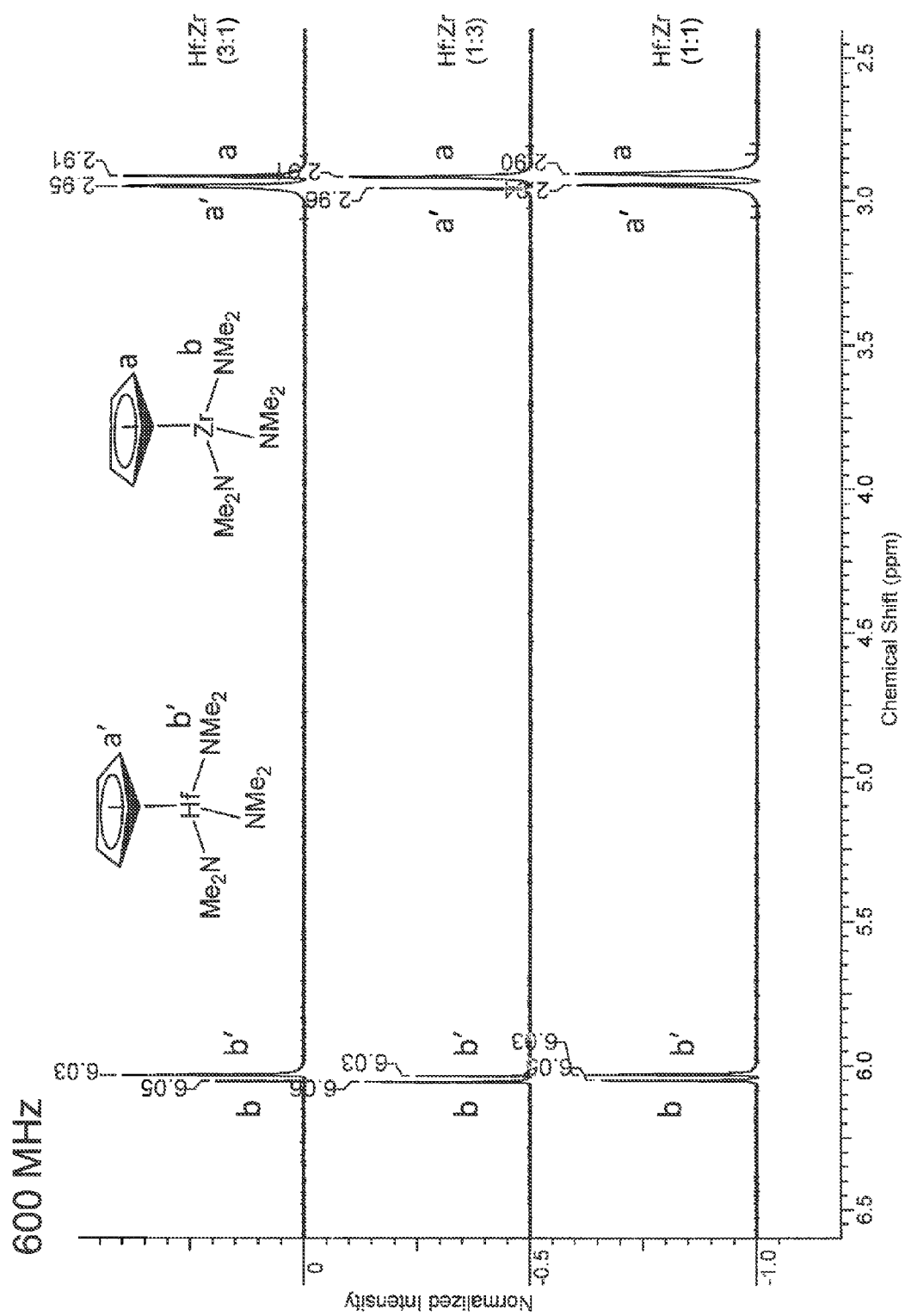
FIG. 6 is 600 MHz $^1H$ NMR spectra of the blends of $ZrCp(NMe_2)_3$ and $Hf(MeCp)(NMe_2)_3$.

1:1, 3:1, and 1:3 blends of ZrCp(NMe$_2$)$_3$ and HfCp (NMe$_2$)$_3$ were prepared by mixing the neat products and stirring for 24 hours. Open cup thermal gravimetric analysis (TGA) and differential scanning calorimetry (DSC) of the mixtures was performed after the 24 hours of stirring. The results are shown in FIG. 3 (TGA) and FIG. 4 (DSC). The inset in FIG. 3 is an enlarged view of the temperature ranging from 230° C. to 240° C. $^1$H NMR spectra at 300 MHz and 600 MHz were also obtained after the 24 hours of stirring. The results are shown in FIG. 5 (300 MHz) and FIG. 6 (600 MHz). As can be seen from these figures, the identity of the two starting materials remains the same and no disproportionation occurs between the two precursors (i.e., none of the NMe$_2$ ligands are replaced by the Cp ligand or vice versa to produce tetrakis(dimethylamino) or bis, tris, or tetrakis (cyclopentadienyl) compounds).

Figure 7:
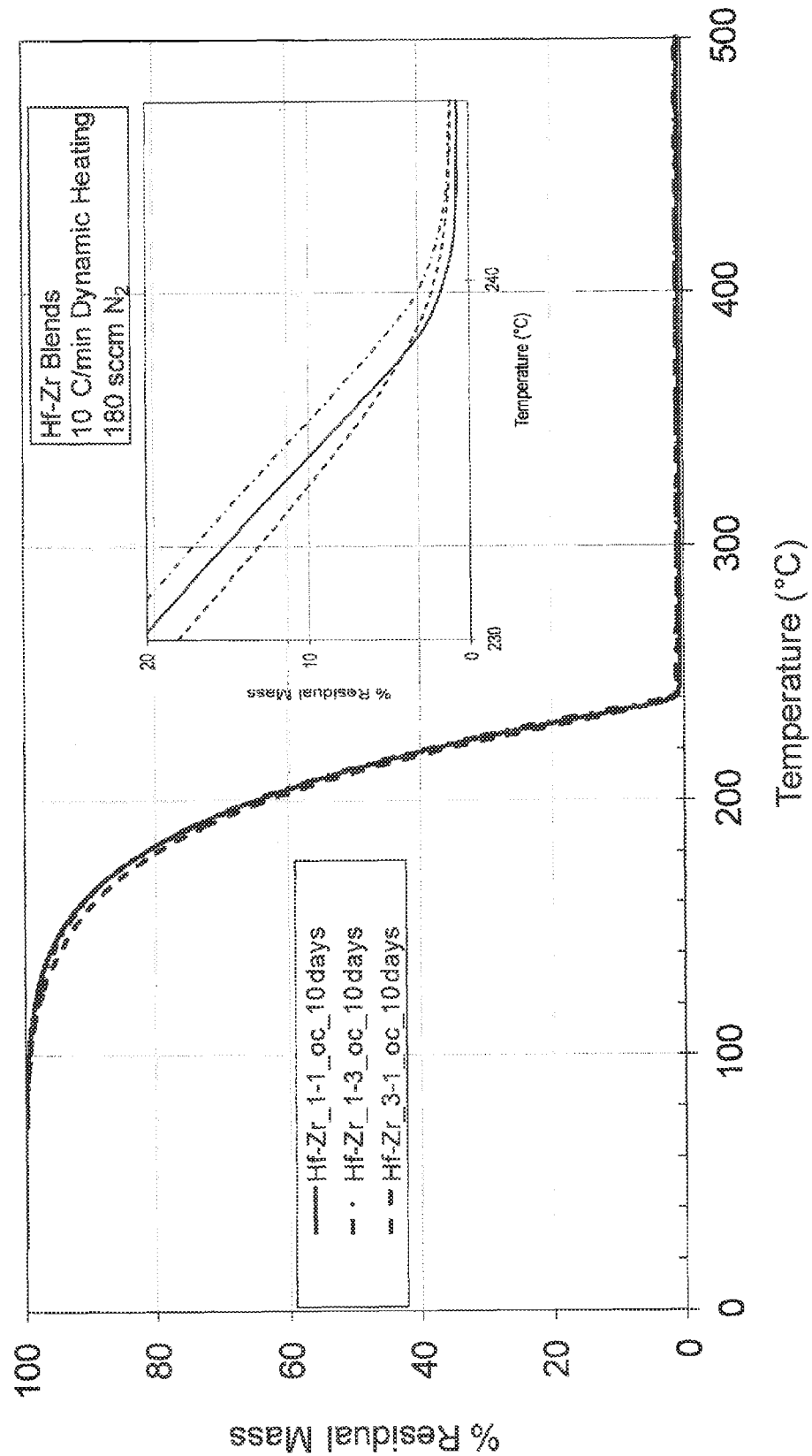
FIG. 7 is a TGA graph showing the percent residual mass versus temperature in open cup configuration for blends of $ZrCp(NMe_2)_3$ and $Hf(MeCp)(NMe_2)_3$ after 10 days at room temperature.

Samples of the 3 blends were subject to TGA testing after 10 days at room temperature. The results are shown in FIG. 7. The inset in FIG. 7 is an enlarged view of the temperature ranging from 230° C. to 245° C. The minor differences between the inset of FIGS. 3 and 7 are the result of instrumentation error. However, no significant differences are observable, indicating stable mixtures.

Figure 8:
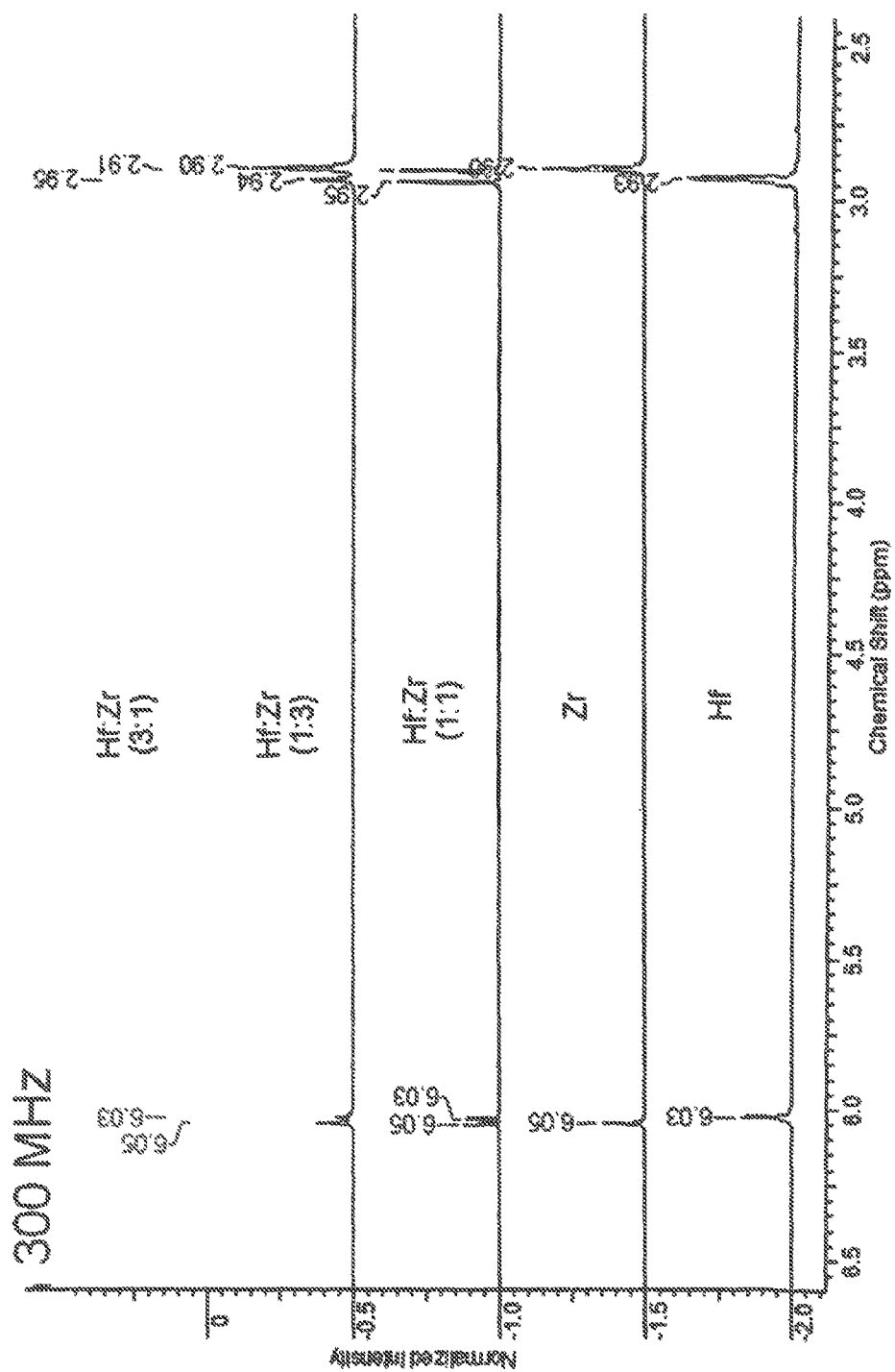
FIG. 8 is 300 MHz $^1H$ NMR spectra of the blends of $ZrCp(NMe_2)_3$ and $Hf(MeCp)(NMe_2)_3$ after 8 hours at 120° C.

Samples of the 3 blends (i.e., 1:1, 3:1, and 1:3) were also subject to thermal stability testing at 120° C. or 150° C. for 8 hours. Additional $^1$H NMR spectra were obtained. The results are shown in FIG. 8 (120° C.) and FIG. 9 (150° C.). Even after heating, the identity of the two starting materials remains the same and no disproportionation occurs between the two precursors.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method of depositing a dielectric film on a substrate, the method comprising introducing into a reaction chamber a vapor of a precursor selected from the group consisting of Zr(MeCp)(NMe$_2$)$_3$, Zr(EtCp)(NMe$_2$)$_3$, ZrCp(NMe$_2$)$_3$, Zr(MeCp)(NEtMe)$_3$, Zr(EtCp)(NEtMe)$_3$, ZrCp(NEtMe)$_3$, Zr(MeCp)(NEt$_2$)$_3$, Zr(EtCp)(NEt$_2$)$_3$, ZrCp(NEt$_2$)$_3$, Zr(iPr$_2$Cp)(NMe$_2$)$_3$, Zr(tBu$_2$Cp)(NMe$_2$)$_3$, Hf(MeCp) (NMe$_2$)$_3$, Hf(EtCp)(NMe$_2$)$_3$, HfCp(NMe$_2$)$_3$, Hf(MeCp) (NEtMe)$_3$, Hf(EtCp)(NEtMe)$_3$, HfCp(NEtMe)$_3$, Hf(MeCp) (NEt$_2$)$_3$, Hf(EtCp)(NEt$_2$)$_3$, HfCp(NEt$_2$)$_3$, Hf(iPr$_2$Cp) (NMe$_2$)$_3$, Hf(tBu$_2$Cp)(NMe$_2$)$_3$, and mixtures thereof; and
depositing the dielectric film on the substrate.

2. The method of claim 1, wherein the dielectric film is M$^1$O$_2$, wherein M$^1$ is Hf, Zr, or mixtures thereof.

3. The method of claim 1, wherein the dielectric film is M$^1$O$_b$N$_c$, wherein $1.5 \leq b \leq 2.5$, $0 < c \leq 0.5$, and M$^1$ is Hf, Zr, or mixtures thereof.

4. The method of claim 1, wherein the dielectric film is (M$^1_{1-a}$M$^2_a$)O$_b$N$_c$, wherein $0 \leq a < 1$; $0 < b \leq 3$; $0 < c \leq 0.5$; M$^1$ is Hf, Zr, or mixtures thereof; and M$^2$ is selected from the group consisting of magnesium (Mg), calcium (Ca), zinc (Zn), boron (B), aluminum (Al), indium (In), silicon (Si), germanium (Ge), tin (Sn), hafnium (Hf), zirconium (Zr), titanium (Ti), vanadium (V), niobium (Nb), tantalum (Ta), a Lanthanide atoms, and a rare-earth atom.

5. The method of claim 1, wherein the dielectric film is (M$^1_{1-a}$M$^2_a$)O$_b$, wherein $0 \leq a < 1$; $0 < b \leq 3$; M$^1$ is Hf, Zr, or mixtures thereof; and M$^2$ is selected from the group consisting of magnesium (Mg), calcium (Ca), zinc (Zn), boron (B), aluminum (Al), indium (In), silicon (Si), germanium (Ge), tin (Sn), hafnium (Hf), zirconium (Zr), titanium (Ti), vanadium (V), niobium (Nb), tantalum (Ta), a Lanthanide atoms, and a rare-earth atom.

6. The method of claim 5, further comprising introducing into a reaction chamber a vapor of a M$^2$ containing precursor to form the (M$^1_{1-a}$M$^2_a$)O$_b$ dielectric film, wherein the M$^2$ containing precursor is an aluminum derivative selected from the group consisting of an alkoxyalane having the formula AlR$^1_x$(OR$^2$)$_{3-x}$, wherein $0 \leq x \leq 3$, R$^1$ represents a linear or branched alkyl group having 1 to 6 carbon atom, and R$^2$ represents a hydrogen atom or a linear or branched alkyl group having 1 to 6 carbon atoms; and an amidoalane having the formula AlR$^3_y$(NR$^4$R$^5$)$_{3-y}$, wherein $0 \leq y \leq 3$ and each R$^3$, R$^4$, and R$^5$ is independently selected from a hydrogen atom or a linear or branched alkyl having 1 to 6 carbon atoms.

7. The method of claim 6, wherein the M$^2$ containing precursor is trimethylaluminum [Al(CH$_3$)$_3$], dimethyl aluminum hydride [AlH(CH$_3$)$_2$], or AlMe$_2$(OiPr).

8. The method of claim 5, further comprising introducing into a reaction chamber a vapor of a M$^2$ containing precursor to form the (M$^1_{1-a}$M$^2_a$)O$_b$ dielectric film, wherein the M$^2$ containing precursor has the following formula:

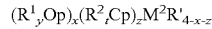

$$(R^1_y Cp)_x (R^2_t Cp)_z M^2 R'_{4-x-z}$$

wherein:
M$^2$ is Ti, Hf, or Zr;
$0 \leq x \leq 3$;
$0 \leq z \leq 3$;
$1 \leq (x+z) \leq 4$;
$0 \leq y \leq 7$;
$0 \leq t \leq 5$;

($R^1{}_y$Op) represents a pentadienyl (Op) ligand substituted by y $R^1$ groups;

($R^2{}_t$Cp) represents a cyclopentadienyl (Cp) ligand substituted by t $R^2$ groups;

each $R^1$ and $R^2$ is independently selected from the group consisting of chlorine; a linear or branched alkyl group having from one to four carbon atoms; a N-alkyl amino group, wherein the alkyl group is linear or branched and has from one to four carbon atoms; a N,N-dialkyl amino group wherein each alkyl group, identical or different from the other, is linear or branched and has from one to four carbon atoms; a linear or branched alkoxy group having from one to four carbon atoms; an alkylsilylamide group; an amidinate group; and a carbonyl group;

each R' is independently selected from the group consisting of hydrogen; fluorine; chlorine; bromine; iodine; a linear or branched alkyl group having from one to four carbon atoms; a N-alkyl amino group, wherein the alkyl group is linear or branched and has from one to four carbon atoms; a N,N-dialkyl amino group, wherein each alkyl group, identical or different from the other, is linear or branched and has from one to four carbon atom; a linear or branched alkoxy group having from one to four carbon atoms; an alkylsilyl amino group, wherein the alkyl group is linear or branched and has from one to four carbon atoms; a dialkylsilyl amino group, wherein each alkyl group, identical or different from the other, is linear or branched and has from one to four carbon atoms; a trialkylsilyl amino group, wherein each alkyl group, identical or different from the other, is linear or branched and has from one to four carbon atoms; an amidinates group; and a carbonyl group.

9. The method of claim 8, wherein the $M^2$ containing precursor is selected from the group consisting of $HfCp_2Cl_2$, $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(EtCp)_2Me_2$, $Hf(MeCp)_2(CO)_2$, $ZrCp_2Cl_2$, $Zr(MeCp)_2Me_2$, $ZrCp(MeCp)Cl_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$, $Zr(MeCp)(NMe_2)_3$, $Zr(EtCp)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)(NEt_2)_3$, $Zr(EtCp)(NEt_2)_3$, $ZrCp(NEt_2)_3$, $Zr(iPr_2Cp)(NMe_2)_3$, $Zr(tBu_2Cp)(NMe_2)_3$, $Hf(MeCp)(NMe_2)_3$, $Hf(EtCp)(NMe_2)_3$, $HfCp(NMe_2)_3$, $Hf(MeCp)(NEtMe)_3$, $Hf(EtCp)(NEtMe)_3$, $HfCp(NEtMe)_3$, $Hf(MeCp)(NEt_2)_3$, $Hf(EtCp)(NEt_2)_3$, $HfCp(NEt_2)_3$, $Hf(iPr_2Cp)(NMe_2)_3$, $Hf(tBu_2Cp)(NMe_2)_3$ and mixtures thereof.

10. The method of claim 5, further comprising introducing into a reaction chamber a vapor of a $M^2$ containing precursor to form the $(M^1{}_{1-a}M^2{}_a)O_b$ dielectric film, wherein the $M^2$ containing precursor is a niobium derivative selected from the group consisting of $Nb(OMe)_5$; $Nb(OEt)_5$; $Nb(NMe_2)_5$; $Nb(NEt_2)_4$; $Nb(NEt_2)_5$; $Nb(OR^{27})_4(O-C(R^{28})(R^{29})-CH_2-OR^{30})$ wherein $R^{27}$, $R^{28}$, $R^{29}$ and $R^{30}$, identical or different, independently represent an hydrogen atom or a linear or branched alkyl having 1 to 6 carbon atoms; $Nb(OR^{31})_4[O-C(R^{32})(R^{33})-CH_2-N(R^{34})(R^{35})]$, wherein $R^{31}$, $R^{32}$, $R^{33}$, $R^{34}$ and $R^{35}$, identical or different, independently represent an hydrogen atom or a linear or branched alkyl having 1 to 6 carbon atoms; and $Nb(=NR^{36})(NR^{37}R^{38})_3$, wherein $R^{36}$, $R^{37}$ and $R^{38}$, identical or different, independently represent an hydrogen atom or a linear or branched alkyl having 1 to 6 carbon atoms.

11. The method of claim 10, wherein the $M^2$ containing precursor is $Nb(OMe)_5$, $Nb(OEt)_5$, $Nb(NMe_2)_5$, $Nb(NEt_2)_4$, $Nb(NEt_2)_5$, or $Nb(OEt)_4(OCMe_2CH_2-OMe)$.

12. The method of claim 5, further comprising introducing into a reaction chamber a vapor of a $M^2$ containing precursor to form the $(M^1{}_{1-a}M^2{}_a)O_b$ dielectric film, wherein the $M^2$ containing precursor is a lanthanide derivative with at least one beta diketonate ligand or at least one cyclopentadienyl ligand.

13. The method of claim 1, wherein the precursor is selected from $ZrCp(NMe_2)_3$, $HfCp(NMe_2)_3$, and mixtures thereof.

14. The method of claim 13, wherein the dielectric film is $M^1O_2$, wherein $M^1$ is Hf, Zr, or mixtures thereof.

15. The method of claim 13, wherein the dielectric film is $(M^1{}_{1-a}M^2{}_a)O_b$, wherein $0 \le a < 1$; $0 < b \le 3$; $M^1$ is Hf, Zr, or mixtures thereof; and $M^2$ is selected from the group consisting of magnesium (Mg), calcium (Ca), zinc (Zn), boron (B), aluminum (Al), indium (In), silicon (Si), germanium (Ge), tin (Sn), hafnium (Hf), zirconium (Zr), titanium (Ti), vanadium (V), niobium (Nb), tantalum (Ta), a Lanthanide atoms, and a rare-earth atom.

16. A method of depositing a dielectric film on a substrate, the method comprising introducing into a reaction chamber a vapor of a precursor selected from the group consisting of $Zr(MeCp)(NMe_2)_3$, $Zr(EtCp)(NMe_2)_3$, $ZrCp(NMe_2)_3$, $Zr(MeCp)(NEtMe$ 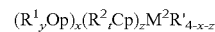 $Zr(EtCp)(NEtMe)_3$, $ZrCp(NEtMe)_3$, $Zr(MeCp)(NEt_2)_3$, $Zr(EtCp)(NEt_2)_3$, $ZrCp(NEt_2)_3$, $Zr(iPr_2Cp)(NMe_2)_3$, $Zr(tBu_2Cp)(NMe_2)_3$, and mixtures thereof; and introducing into a reaction chamber a vapor of a $M^2$ containing precursor, wherein the $M^2$ containing precursor has the following formula:

$$(R^1{}_yOp)_x(R^2{}_tCp)_zM^2R'_{4-x-z}$$

wherein:
$M^2$ is Ti or Hf;
$0 \le x \le 3$;
$0 \le z \le 3$;
$1 \le (x+z) \le 4$;
$0 \le y \le 7$;
$0 \le t \le 5$;

($R^1{}_y$Op) represents a pentadienyl (Op) ligand substituted by y $R^1$ groups;

($R^2{}_t$Cp) represents a cyclopentadienyl (Cp) ligand substituted by t $R^2$ groups;

each $R^1$ and $R^2$ is independently selected from the group consisting of chlorine; a linear or branched alkyl group having from one to four carbon atoms; a N-alkyl amino group, wherein the alkyl group is linear or branched and has from one to four carbon atoms; a N,N-dialkyl amino group wherein each alkyl group, identical or different from the other, is linear or branched and has from one to four carbon atoms; a linear or branched alkoxy group having from one to four carbon atoms; an alkylsilylamide group; an amidinate group; and a carbonyl group;

each R' is independently selected from the group consisting of hydrogen; fluorine; chlorine; bromine; iodine; a linear or branched alkyl group having from one to four carbon atoms; a N-alkyl amino group, wherein the alkyl group is linear or branched and has from one to four carbon atoms; a N,N-dialkyl amino group, wherein each alkyl group, identical or different from the other, is linear or branched and has from one to four carbon atom; a linear or branched alkoxy group having from one to four carbon atoms; an alkylsilyl amino group, wherein the alkyl group is linear or branched and has from one to four carbon atoms; a dialkylsilyl amino group, wherein each alkyl group, identical or different from the other, is linear or branched and has from one to four carbon atoms; a trialkylsilyl amino group, wherein each alkyl group, identical or different from the other, is linear or branched and has from one to four carbon atoms; an amidinates group; and a carbonyl group; and depositing the dielectric film on the substrate.

17. The method of claim 16, wherein the $M^2$ containing precursor is $HfCp_2Cl_2$, $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(EtCp)_2Me_2$, $Hf(MeCp)_2(CO)_2$, $Hf(MeCp)(NMe_2)_3$, $Hf(EtCp)(NMe_2)_3$, $HfCp(NMe_2)_3$, $Hf(MeCp)(NEtMe)_3$, $Hf(EtCp)(NEtMe)_3$, $HfCp(NEtMe)_3$, $Hf(MeCp)(NEt_2)_3$, $Hf(EtCp)(NEt_2)_3$, $HfCp(NEt_2)_3$, $Hf(iPr_2Cp)(NMe_2)_3$, $Hf(tBu_2Cp)(NMe_2)_3$ and mixtures thereof.

18. The method of claim 16, wherein the $M^2$ containing precursor is $Nb(OMe)_5$, $Nb(OEt)_5$, $Nb(NMe_2)_5$, $Nb(NEt_2)_4$, $Nb(NEt_2)_5$, or $Nb(OEt)_4(OCMe_2CH_2—OMe)$.

19. A method of depositing a dielectric film on a substrate, the method comprising introducing into a reaction chamber a vapor of a precursor selected from the group consisting of $Zr(MeCp)(NMe_2)_3$, $Zr(EtCp)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)(NEt_2)_3$, $Zr(EtCp)(NEt_2)_3$, $ZrCp(NEt_2)_3$, $Zr(iPr_2Cp)(NMe_2)_3$, $Zr(tBu_2Cp)(NMe_2)_3$, $Hf(MeCp)(NMe_2)_3$, $Hf(EtCp)(NMe_2)_3$, $HfCp(NMe_2)_3$, $Hf(MeCp)(NEtMe)_3$, $Hf(EtCp)(NEtMe)_3$, $HfCp(NEtMe)_3$, $Hf(MeCp)(NEt_2)_3$, $Hf(EtCp)(NEt_2)_3$, $HfCp(NEt_2)_3$, $Hf(iPr_2Cp)(NMe_2)_3$, $Hf(tBu_2Cp)(NMe_2)_3$, and mixtures thereof; and introducing into a reaction chamber a vapor of a $M^2$ containing precursor, wherein the $M^2$ containing precursor is a niobium derivative selected from the group consisting of $Nb(OMe)_5$; $Nb(OEt)_5$; $Nb(NMe_2)_5$; $Nb(NEt_2)_4$; $Nb(NEt_2)_5$; $Nb(OR^{27})_4(O—C(R^{28})(R^{29})—CH_2—OR^{30})$, wherein $R^{27}$, $R^{28}$, $R^{29}$ and $R^{30}$, identical or different, independently represent a hydrogen atom or a linear or branched alkyl group having 1 to 6 carbon atoms; $Nb(OR^{31})_4[O—C(R^{32})(R^{33})—CH_2—N(R^{34})(R^{35})]$, wherein $R^{31}$, $R^{32}$, $R^{33}$, $R^{31}$ and $R^{35}$, identical or different, independently represent a hydrogen atom or a linear or branched alkyl group having 1 to 6 carbon atoms; and $Nb(=NR^{36})(NR^{37}R^{38})_3$, wherein $R^{36}$, $R^{37}$ and $R^{38}$, identical or different, independently represent a hydrogen atom or a linear or branched alkyl group having 1 to 6 carbon atoms; and depositing the dielectric film on the substrate.

* * * * *